United States Patent [19]
Diaz et al.

[11] Patent Number: 5,981,776
[45] Date of Patent: Nov. 9, 1999

[54] HETEROCYCLIC BIARYL COMPOUNDS, PHARMACEUTICAL AND COSMETIC COMPOSITIONS CONTAINING THEM AND USES THEREOF

[75] Inventors: Philippe Diaz, Nice; Bruno Charpentier, Biot, both of France

[73] Assignee: Centre International de Recherches Dermatologiques Galderma, Valbonne, France

[21] Appl. No.: 08/930,796

[22] PCT Filed: Feb. 4, 1997

[86] PCT No.: PCT/FR97/00217

§ 371 Date: Nov. 24, 1997

§ 102(e) Date: Nov. 24, 1997

[87] PCT Pub. No.: WO97/29100

PCT Pub. Date: Aug. 14, 1997

[30] Foreign Application Priority Data

Feb. 6, 1996 [FR] France ................................ 96 01424

[51] Int. Cl.$^6$ .................................................. C07D 307/78
[52] U.S. Cl. .................... 549/462; 514/415; 514/469; 540/1; 546/201; 546/277.4
[58] Field of Search ................................. 514/469, 415; 424/59; 549/462; 540/1; 546/201, 277.4

[56] References Cited

U.S. PATENT DOCUMENTS 3,917,654 11/1975 Petracek ................................ 260/346.2
4,704,462 11/1987 Chang et al. ............................ 549/466

FOREIGN PATENT DOCUMENTS 0 322 004  6/1989  European Pat. Off. .
0 470 039  7/1991  European Pat. Off. .
0 526 951  2/1993  European Pat. Off. .
96/03396   2/1996  WIPO .

OTHER PUBLICATIONS

Chem. Abstr. 115 : 8229 v 1991.
Chemical Abstracts, vol. 113, p. 706, 1990.

*Primary Examiner*—Cecilia J. Tsang
*Assistant Examiner*—David Lukton
*Attorney, Agent, or Firm*—Burns, Doane, Swecker & Mathis, L.L.P.

[57] ABSTRACT

The invention relates to novel heterocyclic biaryl compounds which have the general formula (I):

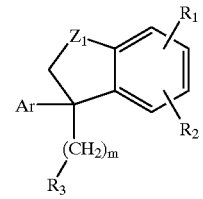

as well as to the use of these compounds in pharmaceutical compositions intended for use in human or veterinary medicine (dermatological, rheumatic, respiratory, cardiovascular and ophthalmological complaints in particular), or alternatively in cosmetic compositions.

27 Claims, 2 Drawing Sheets

X: halogen
Z₁: hetero atom

HETEROCYCLIC BIARYL COMPOUNDS, PHARMACEUTICAL AND COSMETIC COMPOSITIONS CONTAINING THEM AND USES THEREOF

BRIEF SUMMARY OF THE INVENTION

The invention relates to heterocyclic biaryl compounds as novel and useful industrial products. It also relates to the use of these novel compounds in pharmaceutical compositions intended for use in human or veterinary medicine, or alternatively in cosmetic compositions.

The compounds according to the invention have pronounced activity in the fields of cell proliferation and differentiation, and find applications more particularly in the topical and systemic treatment of dermatological complaints associated with a disorder of keratinization, dermatological (or other) complaints with an inflammatory and/or immunoallergic component, and dermal or epidermal proliferations, these being either benign or malignant. These compounds may also be used in the treatment of degenerative diseases of connective tissue, to combat ageing of the skin, both light-induced and chronological ageing, and to treat disorders of cicatrization. They moreover find an application in the ophthalmological field, in particular in the treatment of corneopathies.

The compounds according to the invention may also be used in cosmetic compositions for body and hair hygiene.

DETAILED DESCRIPTION OF THE INVENTION

Figure 1:
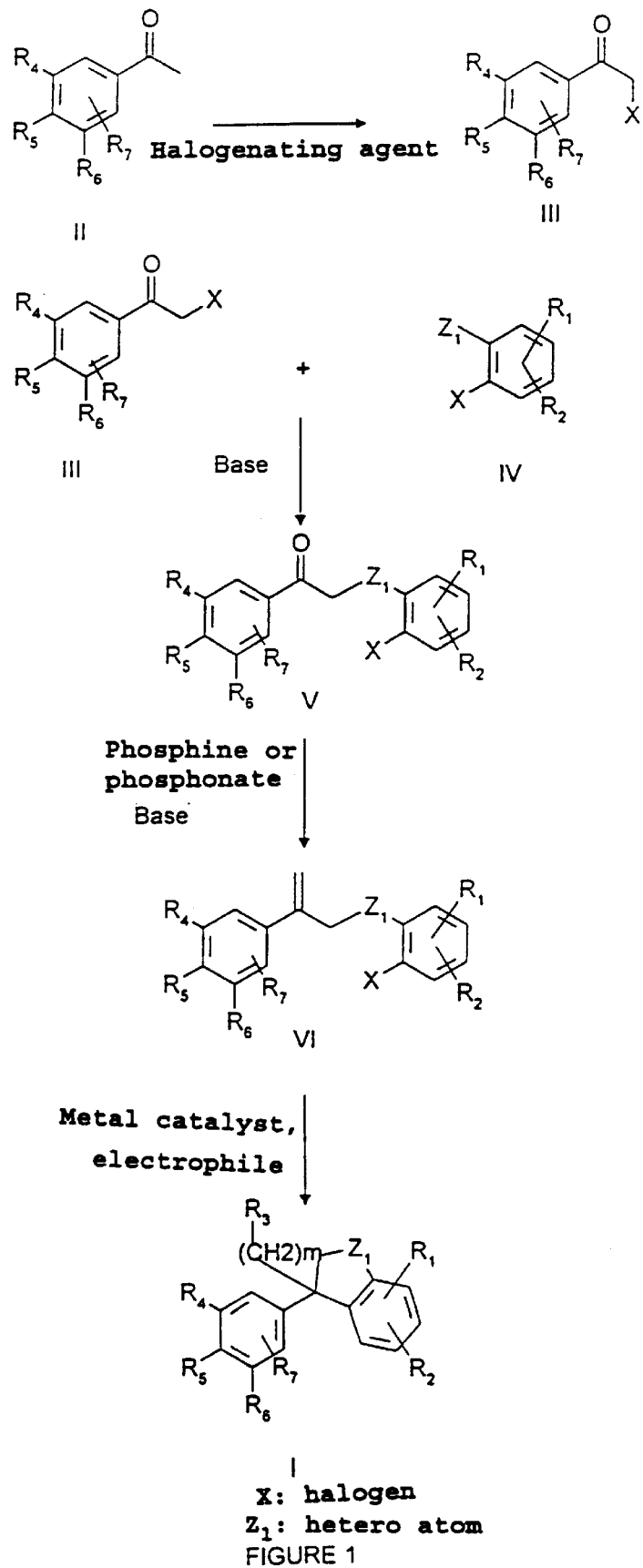
FIG. 1 schematically depicts a reaction scheme for synthesis of compounds according to the invention.

The compounds according to the invention may be represented by the general formula (I) below:

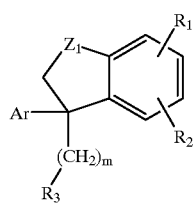

(I)

in which:

Ar represents
either the radical of formula (II) below:

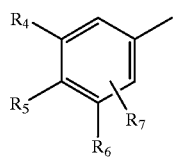

(II)

or the radical of formula (III) below:

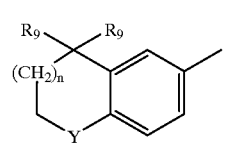

(III)

or the radical of formula (IV) below:

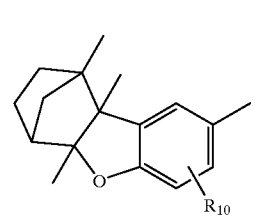

(IV)

$R_1$ represents an atom or a radical chosen from
(i) the $-CH_3$ radical,
(ii) the radical $-(CH_2)_p-O-R_{11}$,
(iii) a radical $-OR_{11}$,
(iv) a radical

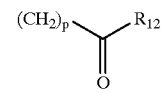

(v) a radical $-S(O)_tR_{13}$,
$R_{11}, R_{12}, R_{13}$, p and t having the meanings given below,
$R_2$ represents a hydrogen atom, a halogen atom, an alkyl radical or the radical $-OR_{11}$,
$R_{11}$ having the meaning given below,
$R_3$ represents an atom or radical chosen from:
(i) an atom or radical chosen from a hydrogen atom, an alkyl radical, an alkenyl radical, an alkynyl radical, an aryl radical, a monohydroxyalkyl or polyhydroxyalkyl radical, a polyether radical, a cyano radical or a radical $-O-R_{11}$,
$R_{11}$ having the meaning given below,
(ii) a radical

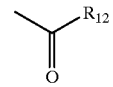

$R_{12}$ having the meaning given below,
(iii) a radical

r and r' having the meaning given below,
$Z_1$ represents O, S or NR',
m is an integer between 0 and 10,
it being understood in all of the preceding text that:
$R_4, R_5, R_6$ and $R_7$, which may be identical or different, are chosen from:
(i) a hydrogen atom, (ii) an alkyl radical having at least 4 carbon atoms, among which the carbon attached to the phenyl radical is substituted with at least two carbon atoms,
(iii) a cycloalkyl radical,
(iv) a radical —$(Z_2)_n$—$(CH_2)_q$—CO—$R_{12}$,
(v) a radical —$Z_3$—$R_{11}$,
with at least one of the radicals $R_4$, $R_5$, $R_6$ and $R_7$ being an alkyl radical as defined in (ii) or a cycloalkyl radical (iii), $Z_2$, $Z_3$, $R_{11}$, $R_{12}$, n and q having the meanings given below, $R_8$ and $R_9$ represent lower alkyl radicals, $R_{10}$ represents a lower alkyl radical, a radical —$OR_{11}$ or a polyether radical, $R_{11}$, which may be identical or different, represents a hydrogen atom, a lower alkyl radical, an aryl radical, an aralkyl radical, a monohydroxyalkyl or polyhydroxyalkyl radical, a polyether radical or a lower acyl radical, $R_{12}$, which may be identical or different, represents:
(a) a hydrogen atom, an alkynyl radical, an alkenyl radical, an alkyl radical or a heterocycle,
(b) a radical

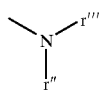

r" and r'" having the meaning given below
(c) a radical —$OR_{13}$ $R_{13}$, which may be identical or different, represents a hydrogen atom, an alkyl radical, a monohydroxyalkyl or polyhydroxyalkyl radical, an optionally substituted aryl or aralkyl radical or a sugar, amino acid or peptide residue, R', which may be identical or different, represents a protecting group for amine functions, a hydrogen atom, a lower alkyl radical, a polyether radical, an optionally substituted aryl radical or an amino acid, peptide or sugar residue, r and r', which may be identical or different, represent protecting groups for amine functions, a hydrogen atom, a lower alkyl radical, a polyether radical, an optionally substituted aryl radical or an amino acid, peptide or sugar residue, or alternatively, taken together, form a heterocycle, r" and r'", which may be identical or different, represent a hydrogen atom, a lower alkyl radical, a polyether radical, an optionally substituted aryl radical or an amino acid, peptide or sugar residue, or alternatively, taken together, form a heterocycle, Y represents $C(R_9)_2$, O, S, Nr', CHOH, CO, SO or $SO_2$, $Z_2$ represents O, S or NR', $Z_3$ represents O or S, n, which may be identical or different, is equal to 0 or 1;
p, which may be identical or different, is equal to 0, 1, 2 or 3; t is equal to 0, 1, 2 or 3; q is an integer between 0 and 10, and the optical and geometrical isomers of the said compounds of formula (I) as well as the salts thereof.

When the compounds according to the invention are in the form of salts, by addition of an acid, these are pharmaceutically or cosmetically acceptable salts obtained by addition of an inorganic or organic acid, in particular hydrochloric acid, sulphuric acid, acetic acid, citric acid, fumaric acid, hemisuccinic acid, maleic acid or mandelic acid. When the compounds according to the invention are in the form of salts by addition of a base, these are salts of an alkali metal or alkaline-earth metal or alternatively of zinc or of an organic amine.

According to the present invention, the term alkyl radical is understood to refer to a linear or branched radical optionally substituted with one or more halogen atoms having from 1 to 20, preferably from 1 to 12, carbon atoms, advantageously methyl, ethyl, isopropyl, butyl, tert-butyl, hexyl, nonyl and dodecyl radicals. When it is lower, the alkyl radical generally comprises from 1 to 12 carbon atoms, preferably from 1 to 4 carbon atoms.

Among the linear alkyl radicals having from 1 to 20 carbon atoms, mention may be made in particular of the methyl, ethyl, propyl, 2-ethylhexyl, octyl, dodecyl, hexadecyl and octadecyl radicals.

Among the branched alkyl radicals having from 1 to 20 carbon atoms, mention may be made in particular of the 2-methylbutyl, 2-methylpentyl, 1-methylhexyl and 3-methylheptyl radicals.

Among the alkyl radicals having at least 4 carbon atoms, in which the carbon attached to the phenyl radical is substituted with at least two carbon atoms, mention may be made of the tert-butyl radical.

The term alkenyl radical is understood to refer to a linear or branched radical having from 1 to 20 carbon atoms and containing one or more double bonds.

Among the alkenyl radicals, a radical containing from 1 to 5 carbon atoms and having one or more ethylenic unsaturations, more particularly such as the allyl radical, is preferred.

The term alkynyl radical is understood to refer to a linear or branched radical having from 1 to 20 carbon atoms and containing one or more triple bonds.

Among the alkynyl radicals, a radical having from 2 to 6 carbon atoms, in particular a propargyl radical, is preferred.

The term lower acyl radical is understood to refer to a radical having from 1 to 6 carbon atoms and preferably the acetyl, propionyl and pivaloyl radicals.

The expression protecting group of an amine function is understood to refer to the corresponding groups described in "Protecting groups in organic synthesis" by T. W. Greene, Ed. by John Wiley and Sons (1981).

The term cycloalkyl radical is understood to refer to a cyclic or polycyclic alkane radical containing from 1 to 10 carbon atoms, optionally substituted with one or more halogen atoms or one or more hydroxyl radicals, and preferably the adamantyl and 1-methylcyclohexyl radicals.

The term polyether radical is understood to refer to a radical having from 1 to 6 carbon atoms and from 1 to 3 oxygen or sulphur atoms, such as the methoxymethyl ether, methoxyethoxymethyl ether or methylthiomethyl ether radicals.

The expression monohydroxyalkyl or polyhydroxyalkyl radical should be understood to refer to a radical containing from 1 to 6 carbon atoms and from 1 to 5 hydroxyl groups.

Among the polyhydroxyalkyl radicals, a radical having from 3 to 6 carbon atoms and from 2 to 5 hydroxyl groups, such as the 2,3-dihydroxypropyl, 2,3,4-trihydroxybutyl or 2,3,4,5-tetrahydroxypentyl radicals or the pentaerythritol residue, is preferred.

Among the optionally substituted aryl radicals, a phenyl radical optionally substituted with at least one halogen atom, a hydroxyl radical, an alkyl radical, a nitro function, a methoxy group or an optionally substituted amine function is preferred.

Among the optionally substituted aralkyl radicals, the benzyl or phenethyl radical optionally substituted with at least one halogen atom, a hydroxyl radical, a nitro function or a methoxy group is preferred.

The term sugar residue is understood to refer to a residue derived in particular from glucose, galactose or mannose, or alternatively from glucuronic acid.

The term amino acid residue is understood to refer in particular to a residue derived from an amino acid such as lysine, glycine or aspartic acid, and the term peptide residue is understood to refer more particularly to a dipeptide or tripeptide residue resulting from the combination of amino acids.

The term heterocycle is understood to refer preferably to a piperidino, morpholino, pyrrolidino or piperazino radical, optionally substituted in position 4 with a $C_1$–$C_6$ alkyl or polyhydroxyalkyl radical as defined above.

The term aminoalkyl radical is understood to refer to a radical preferably containing from 1 to 6 carbon atoms, in particular the aminomethyl, 3-aminopropyl and 6-aminohexyl radicals.

Among the cycloaliphatic radicals of C3 to C6 carbon atoms, mention may be made more particularly of the cyclopropyl and cyclohexyl radicals.

Among the halogen atoms, fluorine or chlorine is preferred.

When the radicals $R_2$ and $R_9$ represent a halogen atom, this is preferably a fluorine, bromine or chlorine atom.

Among the compounds of formula (I) above which fall within the scope of the present invention, mention may be made in particular of the following:

3-[3-(1-adamantyl)-4-methoxyphenyl]-3-methyl-2H-1-benzofuran-6-carboxylic acid, methyl 3-[3-(1-adamantyl)-4-methoxyphenyl]-3-methyl-2H-1-benzofuran-6-carboxylate, 3-[3-(1-adamantyl)-4-methoxyphenyl)]-3-methyl-2H-1-benzofuran-5-carboxylic acid, methyl 3-[3-(1-adamantyl)-4-methoxyphenyl)]-3-methyl-2H-1-benzofuran-5-carboxylate, 3-methyl-3-(5,6,7,8-tetrahydro-5,5,8,8-tetramethyl-2-naphthyl)-2H-1-benzofuran-6-carboxylic acid, methyl 3-methyl-3-(5,6,7,8-tetrahydro-5,5,8,8-tetramethyl-2-naphthyl)-2H-1-benzofuran-6-carboxylate, 3-(propen-2-yl)-3-(5,6,7,8-tetrahydro-5,5,8,8-tetramethyl-2-naphthyl)-2H-1-benzofuran-6-carboxylic acid, methyl 3-(propen-2-yl)-3-(5,6,7,8-tetrahydro-5,5,8,8-tetramethyl-2-naphthyl)-2H-1-benzofuran-6-carboxylate, 3-(propen-2-yl)-3-(5,6,7,8-tetrahydro-5,5,8,8-tetramethyl-2-naphthyl)-2H-1-benzofuran-5-carboxylic acid, methyl 3-(propen-2-yl)-3-(5,6,7,8-tetrahydro-5,5,8,8-tetramethyl-2-naphthyl)-2H-1-benzofuran-5-carboxylate, 3-methyl-3-(5,6,7,8-tetrahydro-5,5,8,8-tetramethyl-2-naphthyl)-2H-1-benzofuran-5-carboxylic acid, methyl 3-methyl-3-(5,6,7,8-tetrahydro-5,5,8,8-tetramethyl-2-naphthyl)-2H-1-benzofuran-5-carboxylate, 3-methyl-3-(1,2,3,4-tetrahydro-1,4a,9b- trimethyl-1,4-methanodibenzofur-8-yl)-2H-1-benzofuran-6-carboxylic acid, methyl 3-methyl-3-(1,2,3,4-tetrahydro-1,4a,9b-trimethyl-1,4-methanodibenzofur-8-yl)-2H-1-benzofuran-6-carboxylate, 3-methyl-3-(1,2,3,4-tetrahydro-1,4a,9b-trimethyl-1,4-methanodibenzofur-8-yl)-2H-1-benzofuran-5-carboxylic acid, methyl 3-methyl-3-(1,2,3,4-tetrahydro-1,4a,9b-trimethyl-1,4-methanodibenzofur-8-yl)-2H-1-benzofuran-5-carboxylate, 3-allyl-3-(5,6,7,8-tetrahydro-5,5,8,8-tetramethyl-2-naphthyl)-2H-1-benzofuran-6-carboxylic acid, methyl 3-allyl-3-(5,6,7,8-tetrahydro-5,5,8,8-tetramethyl-2-naphthyl)-2H-1-benzofuran-6-carboxylate,

[3-(5,6,7,8-tetrahydro-5,5,8,8-tetramethyl-2-naphthyl)-3-methyl-2H-1-benzofuran-5-oyl]morpholine, N-4-hydroxyphenyl-3-(5,6,7,8-tetrahydro- 5,5,8,8-tetramethyl-2-naphthyl)-3-methyl-2H-1-benzofuran-5-carboxamide, N-butyl-3-methyl-3-(5,5,8,8-tetramethyl-5,6,7,8-tetrahydronaphth-2-yl)-2H-1-benzofuran-5-carboxamide, methyl 3-[4-(1-adamantyl)-3-methoxyphenyl-3-methyl-2H-1-benzofuran]-6-carboxylate, 3-[4-(1-adamantyl)-3-methoxyphenyl-3-methyl-2H-1-benzofuran]-6-carboxylic acid, methyl 3-(3-methyl-5,6,7,8-tetrahydro-5,5,8,8-tetramethyl-2-naphthyl)-3-methyl-2H-1-benzofuran-6-carboxylate, 3-(3-methyl-5,6,7,8-tetrahydro-5,5,8,8-tetramethyl-2-naphthyl)-3-methyl-2H-1-benzofuran-6-carboxylic acid, methyl 3-(5,6,7,8-tetrahydro-5,5,8,8-tetramethyl-2-naphthyl)-3-(3,5-di-tert-butyl-4-hydroxybenzyl)-2H-1-benzofuran-6-carboxylate, 3-(5,6,7,8-tetrahydro-5,5,8,8-tetramethyl-2-naphthyl)-3-(3,5-di-tert-butyl-4-hydroxybenzyl)-2H-1-benzofuran-6-carboxylic acid, 3-(5,6,7,8-tetrahydro-5,5,8,8-tetramethyl-2-naphthyl)-3-methyl-2H-1-benzofuran-5-methanol, 3-(5,6,7,8-tetrahydro-5,5,8,8-tetramethyl-2-naphthyl)-3-methyl-2H-1-benzofuran-5-carbaldehyde, methyl (−)-3-(5,6,7,8-tetrahydro-5,5,8,8-tetramethyl-2-naphthyl)-3-methyl-2H-1-benzofuran-5-carboxylate, methyl (+)-3-(5,6,7,8-tetrahydro-5,5,8,8-tetramethyl-2-naphthyl)-3-methyl-2H-1-benzofuran-5-carboxylate, methyl (−)-3-(5,6,7,8-tetrahydro-5,5,8,8-tetramethyl-2-naphthyl)-3-methyl-2H-1-benzofuran-6-carboxylate, methyl (+)-3-(5,6,7,8-tetrahydro-5,5,8,8-tetramethyl-2-naphthyl)-3-methyl-2H-1-benzofuran-6-carboxylate, methyl 3-(5,6,7,8-tetrahydro-5,5,8,8-tetramethyl-2-naphthyl)-3-(2-hexenyl)-2H-1-benzofuran-6-carboxylate, 3-(5,6,7,8-tetrahydro-5,5,8,8-tetramethyl-2-naphthyl)-3-(2-hexenyl)-2H-1-benzofuran-6-carboxylic acid, 3-(5,6,7,8-tetrahydro-5,5,8,8-tetramethyl-2-naphthyl)-3-hexyl-2H-1-benzofuran-6-carboxylic acid, methyl 3-methoxycarbonylmethyl-3-(5,5,8,8-tetramethyl-5,6,7,8-tetrahydronaphth-2-yl)-2H-1-benzofuran-6-carboxylate, 3-carboxymethyl-3-(5,5,8,8-tetramethyl-5,6,7,8-tetrahydronaphth-2-yl)-2H-1-benzofuran-6-carboxylic acid.

According to the present invention, the compounds of formula (I) which are more particularly preferred are those for which at least one, and preferably all, of the conditions below are respected:

$R_1$ is a radical $—(CH_2)_p—CO—O—R_{13}$
$R_2$ is a hydrogen
$R_3$ is a hydrogen or a n alkenyl radical
$R_5$ or $R_6$ is a radical $—OR_{11}$
$R_7$ is a cycloalkyl radical
$Z_1$ is an oxygen atom
Y is a radical $Cr(R_9)_2$
m is equal to 1.

Figure 2:
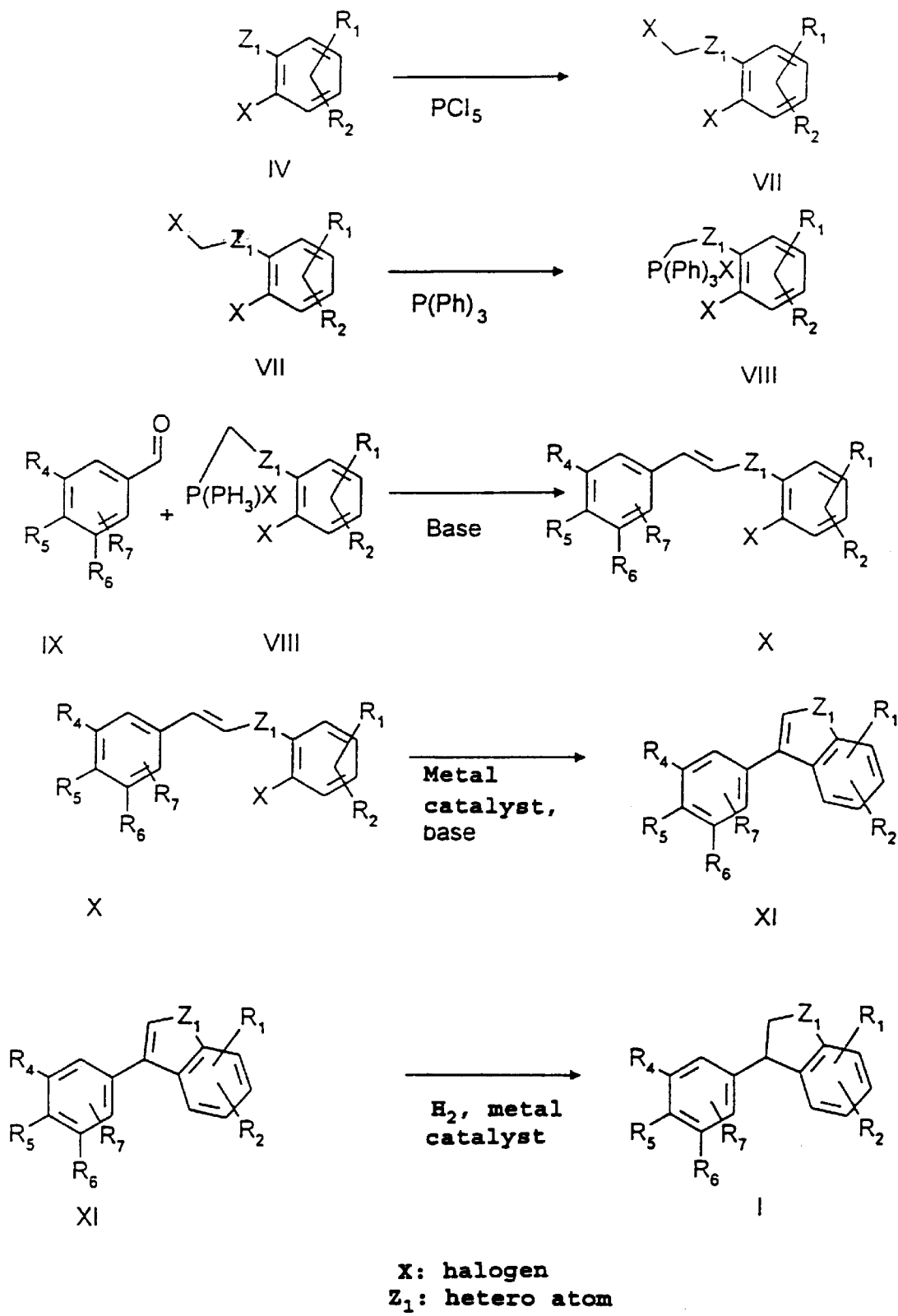
FIG. 2 also schematically depicts a reaction scheme for synthesis of compounds according to the invention.

The subject of the present invention is also processes for the preparation of the compounds of formula (I), in particular according to the reaction schemes given in FIGS. 1 and 2.

Thus, the compounds of general formula (I) may be obtained (FIG. 1) from the ketone II by halogenation, for example using a brominating agent such as bromine. The compound III obtained is then coupled with the compound IV, in the presence of a base such as potassium carbonate or sodium hydride. The coupled derivative V is subjected to the action of a phosphine or a phosphonate in the presence of a base, in order to lead to the compound VI. The compound VI is cyclized by the action of a metal catalyst such as palladium diacetate, in the presence of a hydride donor such as formic acid or of a nucleophile such as vinyltributyltin or lithium acetate and, if necessary, a base.

The addition of silver zeolites or salts such as $Ag_3PO_4$ and of chiral phosphines such as binap makes it possible to induce an asymmetric cyclization.

The compounds of general formula (I) may thus be obtained according to the synthetic scheme of FIG. 2. Compound VII is obtained by halogenation of the product IV with phosphorus pentachloride, for example. It is converted into the phosphonium salt VIII by the action of triphenylphosphine (according to patent EP 428,423 A2). This is coupled with an aldehyde or a ketone IX, by the action of a base such as sodium methoxide or sodium hydride in order to give the enol ether X. It is cyclized in the presence of a metal catalyst such as palladium diacetate, in the presence of a base such as tributylamine, in order to give the product XI. The compound of formula (I) is obtained after hydrogenation of the product XI.

The products of general formula (I) thus obtained may serve as starting materials for the manufacture of other products of general formula (I). These derivatives will be obtained according to the standard synthetic methods employed in chemistry, such as those described in "Advanced Organic Chemistry" by J. March; John Wiley and Sons, 1985.

For example, functional modifications of the group $R_1$ may be carried out as indicated below:

| | |
|---|---|
| carboxylic acid | → ester |
| ester | → carboxylic acid |
| acid | → acid chloride |
| acid chloride | → amide |
| acid | → amide |
| acid | → alcohol |
| alcohol | → aldehyde |
| amide | → amine |
| thiol | → thioether |
| thioether | → sulphoxide |
| thioether | → sulphone |
| sulphonic acid | → sulphonic ester |
| sulphonic acid | → sulphonamide |
| sulphinic acid | → sulphinic ester |

The compounds according to the invention show activity in the test of differentiation Of mouse embryonic teratocarcinoma cells (F9) (Cancer Research 43, pp. 5268, 1983) and/or in the test of inhibition of ornithine decarboxylase after induction with TPA in mice (Cancer Research 38, pp. 793–801, 1978). These tests show the activities of these compounds in the fields of cell differentiation and cell proliferation respectively. In the test of cell (F9) differentiation, an agonist activity may be evaluated as an antagonist activity to retinoic acid receptors. This is because an antagonist is inactive when it is alone in this test, but partially or totally inhibits the effect produced by a retinoid which is an agonist towards the morphology and secret ion of the plasminogen activator. Some of these compounds are thus also active in a test which consists in identifying the molecules which are RAR antagonists, as described in French patent application No. 95/07302 filed on Jun. 19, 1995 by the Applicant. This test comprises the following steps: (i) a sufficient amount of an RAR-agonist molecule is applied topically to a part of the skin of a mammal, (ii) a molecule capable of exhibiting RAR-antagonist activity is administered systemically or topically to this same mammal or to this same part of the skin of the mammal, before, during or after step (i), and (iii) the response on that part of the mammal's skin thus treated is evaluated. Thus, the response to a topical application, to the ear of a mammal, of an RAR-agonist molecule, which corresponds to an increase in the thickness of this ear, may be inhibited by the systemic or topical administration of an RAR-antagonist molecule. In addition, some of these compounds may provide synergism to the biological activity of products binding to the nuclear receptors.

The subject of the present invention is also, as medicinal product, the compounds of formula (I) as defined above.

The compounds according to the invention are particularly suitable in the following fields of treatment:

1) for treating dermatological complaints associated with a keratinization disorder which has a bearing on differentiation and on proliferation, in particular for treating common acne, comedones, polymorphonuclear leukocytes, acne rosacea, nodulocystic acne, acne conglobata, senile acne and secondary acnes such as solar acne, medication-induced acne or occupational acne, 2) for treating other types of keratinization disorders, in particular ichthyosis, ichthyosiform states, Darier's disease, palmoplantar keratoderma, leucoplasias and leucoplasiform states, and cutaneous or mucous (buccal) lichen, 3) for treating other dermatological complaints associated with a keratinization disorder having an inflammatory and/or immunoallergic component and, in particular, all forms of psoriasis, whether it is cutaneous, mucous or ungual psoriasis, and even psoriatic rheumatism, or alternatively cutaneous atopy, such as eczema, or respiratory atopy or alternatively gingival hypertrophy; the compounds may also be used in certain inflammatory complaints which do not exhibit a disorder of keratinization, 4) for treating all dermal or epidermal proliferations, whether benign or malignant and whether or not they are of viral origin, such as common warts, flat warts and verruciform epidermodysplasia, it being also possible for the oral or florid papillomatoses and the proliferations to be induced by ultraviolet radiation, in particular in the case of basocellular and spinocellular epithelioma, 5) for treating other dermatological disorders such as bullosis and collagen diseases, 6) for treating certain ophthalmological disorders, in particular corneopathies, 7) for repairing or combating both light-induced and chronological ageing of the skin or for reducing actinic keratoses and pigmentations, or any pathology associated with chronological or actinic ageing, 8) for preventing or curing the stigmata of epidermal and/or dermal atrophy induced by local or systemic corticosteroids, or any other form of skin atrophy, 9) for preventing or treating cicatrization disorders or for preventing or repairing vibices, 10) for combating disorders of sebaceous functioning such as the hyperseborrhoea of acne or simple seborrhoea, 11) in the treatment or prevention of cancerous or precancerous states, 12) in the treatment of inflammatory complaints such as arthritis, 13) in the treatment of any complaint of viral origin on the skin or generally, such as Kaposi's syndrome, 14) in the prevention or treatment of alopecia, 15) in the treatment of dermatological or general complaints having an immunological component, 16) in the treatment of complaints of the cardiovascular system such as arteriosclerosis, 17) in the treatment of skin disorders due to exposure to UV radiation.

In the therapeutic fields mentioned above, the compounds according to the invention may advantageously be employed in combination with other compounds having retinoid-type activity, with D vitamins or derivatives thereof, with corticosteroids, with anti-free-radical agents, α-hydroxy or α-keto acids or derivatives thereof, or alternatively with ion-channel blockers. The expression D vitamins or derivatives thereof is understood to refer, for example, to vitamin $D_2$ or $D_3$ derivatives and in particular 1,25-dihydroxy vitamin $D_3$. The expression anti-free-radical agent is understood to refer, for example, to α-tocopherol, superoxide dismutase, ubiquinol or certain metal-chelating agents. The expression α-hydroxy or α-keto acids or derivatives thereof is understood to refer, for example, to lactic acid, malic acid, citric acid, glycolic acid, mandelic acid, tartaric acid, glyceric acid or ascorbic acid or salts, amides or esters thereof. Lastly, the expression ion-channel blockers is understood to refer, for example, to Minoxidil (2,4-diamino-6-piperidinopyrimidine 3-oxide) and derivatives thereof.

The subject of the present invention is also medicinal compositions containing at least one compound of formula (I) as defined above, one of the optical or geometrical isomers thereof or one of the salts thereof.

The subject of the present invention is thus a novel medicinal composition intended in particular for treating the abovementioned complaints, and which is characterized in that it comprises, in a pharmaceutically acceptable support which is compatible with the mode of administration selected for this composition, at least one compound of formula (I), one of the optical or geometric isomers thereof or one of the salts thereof.

The compounds according to the invention may be administered enterally, parenterally, topically or ocularly.

Via the enteral route, the medicinal products may be in the form of tablets, gelatin capsules, sugar-coated tablets, syrups, suspensions, solutions, powders, granules, emulsions, microspheres or nanospheres or polymeric or lipid vesicles which allow controlled release. Via the parenteral route, the compositions may be in the form of solutions or suspensions for infusion or for injection.

The compounds according to the invention are generally administered at a daily dose of about 0.01 mg/kg to 100 mg/kg of body weight, taken in 1 to 3 doses.

Via the topical route, the pharmaceutical compositions based on compounds according to the invention are more particularly intended for treating the skin and mucous membranes and may, in this case, be in the form of ointments, creams, milks, salves, powders, impregnated pads, solutions, gels, sprays, lotions or suspensions. They may also be in the form of microspheres or nanospheres or polymeric or lipid vesicles or polymeric patches and hydrogels which allow controlled release. These topical-route compositions may moreover be either in anhydrous form or in an aqueous form, depending on the clinical indication.

Via the ocular route, they are mainly eyedrops.

These compositions for topical or ocular use contain at least one compound of formula (I) as defined above, or one of the optical or geometric isomers thereof, or alternatively one of the salts thereof, at a concentration preferably of between 0.001% and 5% by weight relative to the total weight of the composition.

The compounds of formula (I) according to the invention also find an application in the cosmetic field, in particular in body and hair hygiene and especially for treating skin-types with a tendency towards acne, for promoting the regrowth of the hair, for combating hair loss, for controlling the greasy appearance of the skin or the hair, in protection against the harmful effects of sunlight or in the treatment of physiologically dry skin-types, and for preventing and/or combating light-induced or chronological ageing.

In the cosmetic field, the compounds according to the invention may also advantageously be employed in combination with other compounds having retinoid-type activity, with D vitamins or derivatives thereof, with corticosteroids, with anti-free-radical agents, α-hydroxy or α-keto acids or derivatives thereof, or alternatively with ion-channel blockers, all of these different products being as defined above.

The present invention is thus also directed towards a cosmetic composition which is characterized in that it comprises, in a cosmetically acceptable support which is suitable for topical application, at least one compound of formula (I) as defined above, or one of the optical or geometric isomers thereof or one of the salts thereof, it being possible for this cosmetic composition to be, in particular, in the form of a cream, a milk, a lotion, a gel, microspheres or nanospheres or polymeric or lipid vesicles, a soap or a shampoo.

The concentration of compound of formula (I) in the cosmetic compositions according to the invention is advantageously between 0.001% and 3% by weight relative to the composition as a whole.

The medicinal and cosmetic compositions according to the invention may also contain inert additives or even pharmacodynamically or cosmetically active additives or combinations of these additives and, in particular, wetting agents; depigmenting agents such as hydroquinone, azelaic acid, caffeic acid or kojic acid; emollients; moisturizing agents such as glycerol, PEG 400, thiamorpholinone and derivatives thereof, or, alternatively, urea; anti-seborrhoea or anti-acne agents such as S-carboxymethylcysteine, S-benzylcysteamine, the salts and the derivatives thereof, or benzoyl peroxide; antibiotics such as erythromycin and esters thereof, neomycin, clindamycin and esters thereof, and tetracyclines; antifungal agents such as ketoconazole or 4,5-polymethylene-3-isothiazolidones; agents for promoting the regrowth of the hair, such as Minoxidil (2,4-diamino-6-piperidinopyrimidine 3-oxide) and derivatives thereof, Diazoxide (7-chloro-3-methyl-1,2,4-benzothiadiazine 1,1-dioxide) and Phenytoin (5,4-diphenylimidazolidine-2,4-dione); non-steroidal anti-inflammatory agents; carotenoids and, in particular, β-carotene; anti-psoriatic agents such as anthraline and derivatives thereof and, lastly, eicosa-5,8,11,14-tetraynoic acid and eicosa-5,8,11-triynoic acid, the esters and the amides thereof.

The compositions according to the invention may also contain flavour-enhancing agents, preserving agents such as para-hydroxybenzoic acid esters, stabilizing agents, moisture regulators, pH regulators, osmotic pressure modifiers, emulsifying agents, UV-A and UV-B screening agents, and antioxidants such as α-tocopherol, butylhydroxyanisole or butylhydroxytoluene.

Several examples of the production of active compounds of formula (I) according to the invention, as well as various solid formulations based on such compounds, will now be given by way of illustration and with no limitation. In the examples, TTN refers to tetramethyltetrahydronaphthyl.

A. EXAMPLES OF COMPOUNDS

Example 1

Process for the preparation of methyl 3-[3-(1-adamantyl)-4-methoxyphenyl]-3-methyl-2H-1-benzofuran-6-carboxylate 4-Iodo-3-hydroxybenzoic acid.

3.6% sodium perchlorate solution is added dropwise to a mixture of 4-hydroxybenzoic acid (2.55 g, 18.5 mmol), sodium hydroxide (0.74 g, 18.5 mmol) and sodium iodide (2.77 g, 18.5 mmol) in methanol (50 ml), at 0° C. The mixture is left stirring for two hours at 0° C. 20 ml of 10% sodium thiosulphate solution are added. After stirring, the mixture is acidified with hydrochloric acid to pH 1. It is extracted with 100 ml of ethyl ether. The organic phase is washed twice with 80 ml of water, dried over magnesium sulphate and concentrated on a rotary evaporator under vacuum at 40° C.

White solid. Mass: 2.71 g. Yield: quantitative. m.p.: 178–185° C.; $^1$H NMR (DMSO, 250 MHz): 7.13 (1H Ar, dd, J=1.08 Hz, J=7.55 Hz), 7.41 (1H Ar, d, J=1.08 Hz), 7.76 (1H Ar, d, J=7.55 Hz), 10.71 (1H, s), 12.96 (1H, s).

Methyl 4-iodo-3-hydroxybenzoate.

A solution of 4-iodo-3-hydroxybenzoic acid (2.71 g, 10 mmol) and sulphuric acid (0.7 ml) in methanol (17 ml) is refluxed for 6 h. 20 ml of water are added and the mixture is basified with sodium bicarbonate until neutral. The mixture is extracted with ethyl ether (60 ml). The organic phase is washed with twice 30 ml of water, dried over magnesium sulphate and concentrated on a rotary evaporator under vacuum at 40° C. The product is purified by flash chromatography on a column of silica (50% ethyl acetate, 50% heptane).

White solid. Mass: 2 g. Yield: 72%. m.p.: 164° C.; $^1$H NMR (CDCl$_3$, 250 MHz): 3.91 (3H, s), 5.70 (1H,s), 7.33 (1H Ar, d, J=8.16 Hz), 7.64 (1H Ar, s), 7.75 (1H Ar, d, J=8.16 Hz).

Methyl 3-[(3-(1-adamantyl)-4-methoxybenzoyl)methyloxy]-4-iodobenzoate.

A solution of 3-(1-adamantyl)-4-methoxybromoacetophenone (2.5 g, 6.86 mmol), methyl 3-hydroxy-4-iodobenzoate (1.9 g, 6.83 mmol) and potassium carbonate (0.95 g, 6.88 mmol) in methyl ethyl ketone (50 ml) is refluxed for five hours. The reaction medium is filtered and 40 ml of water and 40 ml of ethyl ether are then added. After stirring and separation of the phases by settling, the organic phase is washed twice with 40 ml of water, dried over magnesium sulphate and concentrated on a rotary evaporator under vacuum at 40° C. The product is purified by flash chromatography on a column of silica (30% ethyl acetate, 70% heptane).

White solid. Mass: 2.52 g. Yield: 66%. m.p.: 156° C.; $^1$H NMR (CDCl$_3$, 250 MHz): 1.77 (6H, s), 2.10 (9H, s), 3.88 (3H, s), 3.92 (3H, s), 5.37 (2H, s), 6.92 (1H Ar, d, J=9.2 Hz), 7.37 to 7.41, (2H Ar, m), 7.87 to 7.92 (3H Ar, m).

Methyl 4-iodo-3-[2-[3-(1-adamantyl)-4-methoxybenzyl]-1-propenyloxy]benzoate

Sodium methoxide (0.94 ml) is added over 8 hours to a mixture of methyl 3-[3-(1-adamantyl)-4-methoxybenzoylmethyloxy]-4-iodobenzoate (2.52 g, 4.49 mmol) and methyltriphenylphosphine bromide (2.45 g) in THF (60 ml).

The mixture is stirred for 12 hours at room temperature. The mixture is concentrated on a rotary evaporator under vacuum at 40° C. It is extracted with 40 ml of ethyl ether and 40 ml of water. After separation of the phases by settling, the organic phase is washed twice with 40 ml of water, dried over anhydrous magnesium sulphate and concentrated on a rotary evaporator under vacuum at 40° C. The product is purified by flash chromatography on a column of silica (60% CH$_2$Cl$_2$, 40% heptane).

White solid. Mass: 1.16 g. Yield: 46%. m.p.: 73° C.; $^1$H NMR (CDCl$_3$, 250 MHz): 1.77 (6H, s), 2.06 (3H, s), 2.10 (6H, s), 3.85 (3H, s), 3.91 (3H, s), 4.98 (2H, s), 5.54 (2H, s), 6.86 (1H Ar, d, J=8.3 Hz), 7.28 to 7.40 (4H Ar, m), 7.51 (1H Ar, d, J=1.7 Hz), 7.86 (1H Ar, d, J=8.1 Hz).

Methyl 3-[3-(1-adamantyl)-4-methoxyphenyl]-3-methyl-2H-1-benzofuran-6-carboxylate A mixture of tributylamine (0.42 g, 2.26 mmol), triphenylphosphine (0.012 g, 0.05 mmol), palladium diacetate (0.005 g, 0.02 mmol) and methyl 4-iodo-3-[2-[3-(1-adamantyl)-4-methoxybenzyl]-1-propenyloxy]benzoate (1.13 g, 2.02 mmol) in acetonitrile (12 ml) is heated at 95° C. for 7 days. For the first 5 days, the reaction mixture is restocked with catalyst and triphenylphosphine. The reaction medium is concentrated on a rotary evaporator under vacuum at 40° C.

20 ml of water and 20 ml of ethyl acetate are added. After separation of the phases by settling, the organic phase is washed twice with 20 ml of water, dried over magnesium sulphate and concentrated on a rotary evaporator under vacuum at 40° C.

The product is purified by flash chromatography on a column of silica (50% CH$_2$Cl$_2$, 50% heptane).

White solid. Mass: 236 mg. Yield: 27%. m.p.: 91–92° C.; $^1$H NMR (CDCl$_3$, 250 MHz): 1.73 (9H, s), 2.03 (9H, s), 3.80 (3H, s), 3.90 (3H, s), 4.48 (1H, d, J=8.68 Hz), 4.61 (1H, d, J=8.68 Hz), 6.78 (1H Ar, d, J=8.52 Hz), 7.03 to 7.14 (3H Ar, m), 7.52 (1H Ar, d, J=1.14 Hz), 7.63 (1H Ar, dd, J=7.79 Hz, J=1.36 Hz). $^{13}$C NMR (CDCl$_3$, 250 MHz): 29.57, 29.24, 37.25, 37.37, 40.65, 49.86, 52.32, 55.21, 86.83, 111.02, 11.53, 123.12, 124.06. 124.79, 124.95, 130.69, 137.08, 138.69, 141.81, 157.72, 159.92, 167.22.

Example 2

Process for the preparation of 3-[3-(1-adamantyl)-4-methoxyphenyl]-3-methyl-2H-1-benzofuran-6-carboxylic acid A mixture of methyl 3-[3-(1-adamantyl)-4-methoxyphenyl]-3-methyl-2H-1-benzofuran-6-carboxylate (62 mg, 0.14 mmol), sodium hydroxide (0.012 g, 0.3 mmol) and lithium hydroxide (0.012 g, 0.28 mmol) is refluxed for 6 h. The mixture is concentrated on a rotary evaporator under vacuum at 40° C. 10 ml of water and 10 ml of ethyl acetate are added. The mixture is acidified with concentrated hydrochloric acid solution to pH=1. After separation of the phases by settling, the organic phase is washed twice with 10 ml of water, dried over magnesium sulphate and concentrated on a rotary evaporator under vacuum at 40° C. The product is purified by flash chromatography on a column of silica (50% $CH_2Cl_2$ 50% EtOAc).

White solid. Mass: 43 mg. Yield: 72%. m.p.: 86° C.; $^1H$ NMR ($CDCl_3$, 250 MHz): 1.75 (9H, s), 2.03 (9H, s), 3.81 (3H, s), 4.50 (1H, d, J=8.68 Hz), 4.63 (1H, d, J=8.68 Hz), 6.79 (1H Ar, d, J=8.50), 7.05 (1H Ar, dd, J=2.27 Hz, J=8.48 Hz), 7.09 to 7.15 (2H Ar, m), 7.59 (1H Ar, 8), 7.70 (1H Ar, dd, J=1.25 Hz, 7.79 Hz). $^{13}C$ NMR ($CDCl_3$, 250 MHz): 25.95, 28.65, 36.66, 36.79, 40.07, 49.32, 54.63, 86.26, 110.95, 123.24, 123.59, 124.22, 124.34, 129.24, 136.35, 138.13, 142.27, 157.17.

Example 3

Process for the preparation of methyl 3-methyl-3-(5,6,7,8-tetrahydro-5,5,8,8-tetramethyl-2-naphthyl)-2H-1-benzofuran-6-carboxylate Methyl 3-[(5,6,7,8-tetrahydro-5,5,8,8-tetramethyl-2-naphthoyl)methyloxy]-4-iodobenzoate.

A solution of 5,6,7,8-tetrahydro-5,5,8,8-tetramethyl-2'-bromoacetonaphthone (1.26 g, 4.1 mmol), methyl 3-hydroxy-4-iodobenzoate (1.15 g, 4.1 mmol) and potassium carbonate (0.62 g, 4.6 mmol) in methyl ethyl ketone (25 ml) is refluxed for three hours. The reaction medium is filtered and then concentrated on a rotary evaporator. 40 ml of water and 40 ml of ethyl acetate are added. After stirring and separation of the phases by settling, the organic phase is washed twice with 40 ml of water, dried over magnesium sulphate and concentrated on a rotary evaporator under vacuum at 40° C. The product is purified by flash chromatography on a column of silica (10% ethyl acetate, 90% heptane).

White solid. Mass: 1.69 g. Yield: 81%. m.p.: 124° C.; $^1H$ NMR ($CDCl_3$, 250 MHz): 1.31 (6H, s), 1.32 (6H, s), 1.71 (4H, s), 3.88 (3H, s), 5.42 (2H, s), 7.35 to 7.41 (2H Ar, m), 7.43 (1H Ar, d, J=8.25 Hz), 7.74 (1H Ar, dd, J=8.25, J=2.5 Hz), 7.90 (1H Ar, d, J=7.5 Hz), 7.98 (1H Ar, d, J=2.5 Hz).

Methyl 4-iodo-3-[2-[5,6,7,8-tetrahydro-5,5,8,8-tetramethyl-2-naphthyl]-1-propenyloxy]benzoate Sodium methoxide (0.62 ml, 3.28 mmol) is added over 8 hours to a mixture of methyl 3-[(5,6,7,8-tetrahydro-5,5,8,8-tetramethyl-2-naphthoyl)methyloxy]-4-iodobenzoate (1.66 g, 3.28 mmol) and methyltriphenylphosphine bromide (1.63 g, 4.56 mmol) in THF (40 ml).

The mixture is stirred for two days at room temperature. The mixture is concentrated on a rotary evaporator under vacuum at 40° C. It is extracted with 40 ml of ethyl ether and 40 ml of water. After separation of the phases by settling, the organic phase is washed twice with 40 ml of water, dried over anhydrous magnesium sulphate and concentrated on a rotary evaporator under vacuum at 40° C. The product is purified by flash chromatography on a column of silica (60% $CH_2Cl_2$, 40% heptane).

White solid. Mass: 0.69 g. Yield: 42%. m.p.: 53° C.; $^1H$ NMR ($CDCl_3$, 250 MHz): 1.29 (6H, s), 1.30 (6H, s), 1.69 (4H, s), 3.91 (3H, s), 4.98 (2H, s), 5.58 (2H, s), 7.20 to 7.41 (4H Ar, m), 7.50 (1H Ar, d, J=1.15 Hz), 7.87 (1H Ar, d, J=8.00). $^{13}C$ NMR ($CDCl_3$, 250 MHz): 31.34, 31.44, 33.71, 33.88, 34.55, 34.69, 51.86, 70.47, 92.84, 112.25, 113.66, 123.01, 123.06, 123.89, 131.08, 135.05, 139.12, 142.01, 144.53, 156.85, 166.05.

Methyl 3-methyl-3-(5,6,7,8-tetrahydro-5,5,8,8-tetramethyl-2-naphthyl)-2H-1-benzofuran-6-carboxylate A mixture of tributylamine (0.5 ml, 2.1 mmol), palladium diacetate (0.03 g, 0.2 mmol), formic acid (0.06 ml, 1.3 mmol) and methyl 4-iodo-3-[2-[5,6,7,8-tetrahydro-5,5,8,8-tetramethyl-2-naphthyl]-1-propenyloxy]benzoate (0.65 g, 1.3 mmol) in acetonitrile (10 ml) is heated at 60° C. for 4 h. The reaction medium is concentrated on a rotary evaporator under vacuum at 40° C. 20 ml of water and 20 ml of ethyl ether are added. After separation of the phases by settling, the organic phase is washed twice with 20 ml of water, dried over magnesium sulphate and concentrated on a rotary evaporator under vacuum at 40° C.

The product is purified by flash chromatography on a column of silica (60% $CH_2Cl_2$, 40% heptane).

White solid. Mass: 330 mg. Yield: 68%. m.p.: 121° C.; $^1H$ NMR ($CDCl_3$, 250 MHz): 1.20 (3H, s), 1.22 (3H, s), 1.25 (6H, s), 1.66 (4H, s), 1.73 (3H, s), 3.91 (3H, s), 4.48 (1H, d, J=8.75 Hz), 4.62 (1H, d, J=8.75 Hz), 7.00 (1H, dd, J=2 Hz, J=8.25 Hz), 7.09 (1H Ar, d, J=8 Hz), 7.18 to 7.24 (2 H Ar, m), 7.52 (1H Ar, s), 7.63 (1H Ar, d, J=8.00 Hz). $^{13}C$ NMR ($CDCl_3$, 250 MHz): 26.16, 31.77, 31.87. 33.96, 34.37, 35.01, 35.10, 49.79, 52.09, 86.48, 110.82, 122.84, 123.67, 123.93, 124.30, 126.60, 130.56, 141.35, 142.15, 143.32, 144.88, 159.80, 166.97.

Example 4

Process for the preparation of 3-methyl-3-(5,6,7,8-tetrahydro-5,5,8,8-tetramethyl-2-naphthyl)-2H-1-benzofuran-6-carboxylic acid A mixture of methyl 3-methyl-3-(5,6,7,8-tetrahydro-5,5,8,8-tetramethyl-2-naphthyl)-2H-1-benzofuran-6-carboxylate (290 mg, 0.77 mmol), sodium hydroxide (0.06 g, 1.54 mmol) and lithium hydroxide (0.06 g, 1.54 mmol) is stirred at room temperature for 24 h. The mixture is concentrated on a rotary evaporator under vacuum at 40° C. 10 ml of water and 10 ml of ethyl acetate are added. The mixture is acidified with concentrated hydrochloric acid solution to pH 1. After separation of the phases by settling, the organic phase is washed twice with 10 ml of water, dried over magnesium sulphate and concentrated on a rotary evaporator under vacuum at 40° C. The product is obtained by recrystallization from a heptane/ethyl ether mixture (3/1).

White solid. Mass: 240 mg. Yield: 86%. m.p.: 206° C.; $^1H$ NMR (DMSO, 250 MHz): 1.17 (6H, s), 1.20 (6H, s), 1.61 (4H, s), 1.70 (3H, s), 4.50 (1H, d, J=9 Hz), 4.65 (1H, d, J=9 Hz), 6.98 (1H, d, J=8.25 Hz), 7.19 to 7.27 (3H Ar, m), 7.34 (1H Ar, s), 7.54 (1H Ar, d, J=7.75 Hz). $^{13}C$ NMR (DMSO, 250 MHz): 25.81, 31.63, 31.73, 33.69, 34.09, 34.63, 34.71, 49.30, 85.43, 110.14, 122.62, 123.50, 123.79, 124.32, 126.56, 131.37, 140.89, 142.63, 142.72, 144.34, 159.37, 167.15.

Example 5

Process for the preparation of methyl 3-methyl-3-(5,6,7,8-tetrahydro-5,5,8,8-tetramethyl-2-naphthyl)-2H-1-benzofuran-5-carboxylate 3-Iodo-4-hydroxybenzoic acid.

3.6% sodium perchlorate solution is added dropwise to a mixture of 4-hydroxybenzoic acid (12.75 g, 0.92 mol), sodium hydroxide (3.7 g, 0.92 mol) and sodium iodide (13.85 g, 0.92 mol) in methanol (350 ml) at 0° C. The mixture is left stirring for two hours at 0° C. 100 ml of 10% sodium thiosulphate solution are added. After stirring, the mixture is acidified with hydrochloric acid to pH 1. It is extracted with 600 ml of ethyl ether. The organic phase is washed twice with 400 ml of water, dried over magnesium sulphate and concentrated on a rotary evaporator under vacuum at 40° C.

White solid. Mass: 28.76 g. Yield: quantitative. m.p.: 157° C.; $^1$H NMR (DMSO, 250 MHz): 6.74 (1H Ar, d, J=8.4 Hz), 7.71 (1H Ar, d, J=8.4 Hz), 8.13 (1H Ar, s), 10.16 (1H, s), 11.12 (1H, s).

Methyl 3-iodo-4-hydroxybenzoate.

A solution of 3-iodo-4-hydroxybenzoic acid (28.76 g, 0.11 mol) and sulphuric acid (6.6 ml) in methanol (160 ml) is refluxed for 6 h. 300 ml of water are added and the mixture is basified with sodium bicarbonate until neutral. It is extracted with ethyl ether (600 ml). The organic phase is washed with twice 400 ml of water, dried over magnesium sulphate and concentrated on a rotary evaporator under vacuum at 40° C. The product is purified by flash chromatography on the column of silica (10% ethyl acetate, 90% $CH_2Cl_2$).

White solid. Mass: 19.1 g. Yield: 63%. m.p.: 153° C.; $^1$H NMR (CDCl$_3$, 250 MHz): 3.89 (3H, s), 7.01 (2H Ar, d, J=8.5 Hz), 7.94 (1H Ar, dd, J=8.5 Hz, J=2 Hz), 8.37 (1H Ar d, J=2 Hz)

Methyl 4-[(5,6,7,8-tetrahydro-5,5,8,8-tetramethyl-2-naphthoyl)methyloxy]3-iodobenzoate.

A solution of 5,6,7,8-tetrahydro-5,5,8,8-tetramethyl-2'-bromoacetonaphthone (9.8 g, 0.032 mol), methyl 4-hydroxy-3-iodobenzoate (8.8 g, 0.032 mol) and potassium carbonate (8.5 g, 0.062 mol) in methyl ethyl ketone (450 ml) is refluxed for 1 day. The reaction medium is filtered and then concentrated on a rotary evaporator. 500 ml of water and 500 ml of ethyl ether are added. After stirring and separation of the phases by settling, the organic phase is washed twice with 500 ml of water, dried over magnesium sulphate and concentrated on a rotary evaporator under vacuum at 40° C. The product is purified by flash chromatography on a column of silica (10% ethyl acetate, 90% heptane).

White solid. Mass: 9.56 g. Yield: 60%. m.p.: 125° C.; $^1$H NMR (CDCl$_3$, 250 MHz): 1.30 (6H, s), 1.32 (6H, s), 1.71 (4H, s), 3.88 (3H, s), 5.40 (2H, s), 6.70 (1H Ar, d, J=8.7 Hz), 7.43 (1H Ar, d, J=8.5 Hz), 7.74 (1H Ar, dd, J=2 Hz, J=8.5 Hz), 7.93 (1H Ar, dd, J=8.7, J=2.3 Hz), 7.98 (1H Ar, d, J=2 Hz), 8.48 (1H Ar, d, J=2.3 Hz).

Methyl 3-iodo-4-[2-(5,6,7,8-tetrahydro-5,5,8,8-tetramethyl-2-naphthyl)-1-propenyloxy]benzoate 30% sodium methoxide solution (2.67 g, 14.83 mmol) is added over 8 hours to a mixture of methyl 4-[(5,6,7,8-tetrahydro-5,5,8,8-tetramethyl-2-naphthoyl)methoxy]-3-iodobenzoate (7.50 g, 14.8 mmol) and methyltriphenylphosphine bromide (7.30 g, 20.42 mmol) in THF (80 ml). The mixture is stirred for 18 hours at room temperature. The mixture is concentrated on a rotary evaporator under vacuum at 40° C. This is extracted with 90 ml of ethyl ether and 90 ml of water. After separation of the phases by settling, the organic phase is washed twice with 90 ml of water, dried over anhydrous magnesium sulphate and concentrated on a rotary evaporator under vacuum at 40° C. The product is purified by flash chromatography on a column of silica (70% $CH_2Cl_2$, 30% heptane).

White solid. Mass: 4.71 g. Yield: 63%. m.p.: 126° C.; $^1$H NMR (CDCl$_3$, 250 MHz): 1.29 (6H, s), 1.30 (6H, s), 1.69 (4H, s), 3.89 (3H, s), 4.99 (2H, s), 5.55 (1H, s), 5.59 (1H, s), 6.87 (1H Ar, d, J=8.7 Hz), 7.21 to 7.33 (2H Ar, m), 7.38 (1H Ar, d, J=1.8 Hz), 8.00 (1H Ar, dd, J=8.7, J=2 Hz), 8.48 (1H Ar, d, J=2 Hz). $^{13}$C NMR (CDCl$_3$, 250 MHz): 31.79, 31.90, 34.16, 34.33, 34.96, 35.10, 52.09, 70.81, 85.85, 111.35, 112.73, 114.05, 123.33, 124.17, 124.46, 126.71, 129.67, 131.45, 131.74, 135.23, 141.06, 141.99, 145.05, 145.10, 160.67, 165.47.

Methyl 3-methyl-3-(5,6,7,8-tetrahydro-5,5,8,8-tetramethyl-2-naphthyl)-2H-1-benzofuran-5-carboxylate A mixture of tributylamine (2.28 ml, 9.6 mmol), palladium diacetate (0.06 g, 0.3 mmol), formic acid (0.29 ml, 7.4 mmol) and methyl 3-iodo-4-[2-[5,6,7,8-tetrahydro-5,5,8,8-tetramethyl-2-naphthyl]-1-propenyloxy]benzoate (1.37 g, 2.72 mmol) in acetonitrile (25 ml) is heated at 95° C. for 4 h. The reaction medium is concentrated on a rotary evaporator under vacuum at 40° C. 40 ml of water and 40 ml of ethyl ether are added. After separation of the phases by settling, the organic phase is washed twice with 20 ml of water, dried over magnesium sulphate and concentrated on a rotary evaporator under vacuum at 40° C.

The product is purified by flash chromatography on a column of silica, (50% $CH_2Cl_2$, 50% heptane).

White solid. Mass: 630 mg. Yield: 61%. m.p.: 74° C.; $^1$H NMR (CDCl$_3$, 250 MHz): 1.20 to 1.24 (12H, m), 1.65 (4H, s), 1.73 (3H, s), 3.83 (3H, s), 4.51 (1H, d, J=8.7 Hz), 4.66 (1H, d, J=8.7 Hz), 6.87 (1H Ar, d, J=8.3 Hz), 6.96 (1H Ar, dd, J=8.3, J=2 Hz), 7.19 to 7.24 (2H Ar, m), 7.73 (1H Ar, d, J=1.8 Hz), 7.92 (1H Ar, dd, J=8.3, J=2 Hz). $^{13}$C NMR (CDCl$_3$ 250 MHz): 26.63, 31.99, 32.08, 32.11, 34.18, 35.21, 35.32, 49.45, 52.04, 87.37, 109.82, 123.31, 123.98, 124.36, 126.46, 126.85, 131.41, 136.62, 142.56, 143.49, 145.04, 163.91, 167.19.

Example 6

Process for the preparation of 3-methyl-3-(5,6,7,8-tetrahydro-5,5,8,8-tetramethyl-2-naphtyl)-2H-1-benzofuran-5-carboxylic acid A mixture of methyl 3-methyl-3-(5,6,7,8-tetrahydro-5,5,8,8-tetramethyl-2-naphthyl)-2H-1-benzofuran-5-carboxylate (510 mg, 1.35 mmol), sodium hydroxide (0.33 g, 7.9 mmol), lithium hydroxide (0.33 g, 7.9 mmol) and water in THF is stirred at room temperature for 5 days. The mixture is concentrated on a rotary evaporator under vacuum at 40° C. 10 ml of water and 10 ml of ethyl acetate are added. The mixture is acidified with concentrated hydrochloric acid solution to pH 1. After separation of the phases by settling, the organic phase is washed twice with 10 ml of water, dried over magnesium sulphate and concentrated on a rotary evaporator under vacuum at 40° C. The solid obtained is washed with heptane.

White solid. Mass: 400 mg. Yield: 83%. m.p.: 246° C.; $^1$H NMR (DMSO, 250 MHz): 1.20 to 1.23 (12H, m), 1.64 (4H, s), 1.74 (3H, s), 3.83 (3H, s), 4.44 (1H, d, J=8.7 Hz), 4.66 (1H, d, J=8.7 Hz), 6.85 (1H Ar, d, J=7.5 Hz), 6.96 (1H Ar, dd, J=8.3, J=2 Hz), 7.19 to 7.24 (2H Ar, m), 7.73 (1H Ar, d, J=1.8 Hz), 7.92 (1H Ar, dd, J=8.3, J=2 Hz). $^{13}$C NMR (DMSO, 250 MHz): 26.26, 31.63, 31.72, 31.75, 33.83, 34.25, 34.96, 35.06, 49.14, 87.01, 109.34, 123.36, 123.74, 124.03, 126.41, 126.52, 131.38, 136.25, 142.39, 143.02, 144.60, 163.59, 167.90.

Example 7

Process for the Preoaration of methyl 3-methyl-3-(1,2,3,4-tetrahydro-1,4a,9b-trimethyl-1,4-methanodibenzofur-8-yl)-2H-1-benzofuran-6-carboxylate 1,2,3,4-Tetrahydro-1,4a,9b-trimethyl-1,4-methanodibenzofuran; (THTMDBF).

50 g (0.267 mmol) of bromoanisole dissolved in 120 ml of ethyl ether are treated at 0° C. with 200 ml of n-butylithium (1.6 M in hexane) and the medium is then left stirring at room temperature overnight. 41.57 g (273 mmol) of (+)-fenchone (Fluka) in 100 ml of ethyl ether are then added dropwise and the mixture is left stirring at room temperature for 6 h. The reaction medium is poured into 200 ml of saturated ammonium chloride solution.

After extraction with 600 ml of ethyl ether, rinsing with water, drying over magnesium sulphate, filtration and evaporation, the residue is chromatographed on silica to give 61.26 g (88%) of 2-O-anisyl-2-endofenchyl alcohol melting at 62–64° C.; αD=+78° (c=1, ethanol).

57.5 g (0.276 mmol) of phosphorus pentachloride are added at −10° C. to a solution of 55.24 g (0.21 mmol) of 2-O-anisyl-2-endofenchyl alcohol and 4 g of calcium carbonate in 800 ml of chloroform.

The reaction mixture is stirred at room temperature for two hours, after which potassium carbonate (30 g) is added and the mixture is filtered. The solid residue is rinsed with chloroform and then chromatographed on silica in a hexane/$CH_2Cl_2$ mixture (9/1) to give 31.5 g (65%) of the expected derivative, melting at 68° C.; αD=−39.5° (c=1, ethanol).

The same synthesis carried out using (−)-fenchone leads to the dextrorotatory isomer of THTMDBF, melting at 68° C.; αD=+36.3° (c=1, ethanol).

1,2,3,4-Tetrahydro-1,4a,9b-trimethyl-1,4-methanodibenzofur-8-yl methyl ketone

A solution containing 22.8 g (0.1 mmol) of (−)-THTMDBF and 7.8 ml (0.11 mmol) of acetyl chloride in 200 ml of dichloromethane is added dropwise to a solution of 14.67 g of aluminium chloride (0.11 mmol) in 150 ml of $CH_2Cl_2$. The reaction medium is left stirring for 4 h and is then poured into ice-water and extracted with $CH_2Cl_2$. After the usual processing of the organic phase, followed by chromatography on silica in a hexane/ethyl ether mixture (85/15), 17.26 g (64%) of the expected derivative, melting at 140–142° C., are isolated; αD=−4.3° (c=1, ethanol).

1,2,3,4-Tetrahydro-1,4a,9b-trimethyl-1,4-methanodibenzofur-8-yl bromomethyl ketone 18 g (66 mmol) of the ketone obtained in Example 3 in 100 ml of dioxane and 100 ml of ether are treated by dropwise addition of a solution of 3.4 ml of bromine in 35 ml of $CH_2Cl_2$. The reaction medium is left stirring for 2 hours at room temperature and is then poured into ice-water and extracted with 800 ml of ethyl ether. After drying and evaporation, the residue is chromatographed on silica in a hexane/$CH_2Cl_2$ mixture (50/50). 19.75 g (80%) of the expected derivative are obtained in the form of an orange-coloured oil.

Methyl 3-(1,2,3,4-tetrahydro-1,4a,9b-trimethyl-1,4-methanodibenzofur-8-oylmethyloxy)-4-iodobenzoate A solution of 1,2,3,4-tetrahydro-1,4a,9b-trimethyl-1,4-methanodibenzofur-8-yl bromomethyl ketone (2.5 g, 6.86 mmol), methyl 3-hydroxy-4-iodobenzoate (1.9 g, 6.83 mmol) and potassium carbonate (0.95 g, 6.88 mmol) in methyl ethyl ketone (50 ml) is refluxed for five hours. The reaction medium is filtered, after which 40 ml of water and 40 ml of ethyl ether are added. After stirring and separation of the phases by settling, the organic phase is washed twice with 40 ml of water, dried over magnesium sulphate and concentrated on a rotary evaporator under vacuum at 40° C. The product is purified by flash chromatography on a column of silica (30% ethyl acetate, 70% heptane).

Colourless oil. Mass: 3.2 g. Yield: 82%. $^1$H NMR ($CDCl_3$, 250 MHz): 0.85 to 1.67 (16H, m), 2.27 (1H, d, J=3.75 Hz), 3.88 (3H, s), 5.36 (2H, s), 6.79 (1H Ar, d, J=8.5 Hz), 7.38 to 7.40 (2H Ar, m), 7.71 (1H Ar, d, J=1.75 Hz), 7.86 to 7.90 (2H Ar, m).

Methyl 4-iodo-3-(1,2,3,4-tetrahydro-1,4a,9b-trimethyl-1,4-methanodibenzofur-8-yl)-1-propenyloxybenzoate.

30% sodium methoxide solution in methanol (1 g, 5.56 mmol) is added dropwise over 8 h, under nitrogen and at room temperature, to a solution of methyl 3-(1,2,3,4-tetrahydro-1,4a,9b-trimethyl-1,4-methanodibenzofur-8-oyl)methyloxy)-4-iodobenzoate (3 g, 5.50 mmol) and methyltriphenylphosphine bromide (2.71 g, 7.58 mmol) in THF (30 ml).

The mixture is left stirring for 8 h at room temperature. The reaction medium is concentrated on a rotary evaporator under vacuum at 40° C. 50 ml of water and 50 ml of ethyl acetate are added. After separation of the phases by settling, the organic phase is washed twice with 50 ml of water, dried over magnesium sulphate and concentrated on a rotary evaporator under vacuum at 40° C. The product is purified by flash chromatography on a column of silica (90% $CH_2Cl_2$, 10% heptane).

Colourless oil. Mass: 2.22 g. Yield: 74%. $^1$H NMR ($CDCl_3$, 250 MHz): 0.87 to 1.66 (16H, m), 2.23 (1H, d, J=3.75 Hz), 3.91 (3H, s), 4.97 (2H, s), 5.51 (2H, s), 7.72 (1H Ar, d, J=8.3 Hz), 7.12 (1H Ar, s), 7.38 (1H Ar, d, J=8.1 Hz), 7.26 (1H Ar, dd, J=1.6 Hz), 7.51 (1H Ar, d, J=1.6 Hz), 7.86 (1H Ar, d, J=8.1 Hz). $^{13}$C NMR ($CDCl_3$, 250 MHz): 17.83, 19.44, 21.75, 23.44, 33.97, 42.12, 49.00, 50.72, 52.17, 55.56, 71.02, 93.15, 97.99, 108.59, 112.53, 112.95, 121.44, 123.31, 126.20, 129.97, 131.34, 133.83, 139.41, 142.18, 157.14, 158.75, 166.39

Methyl 3-methyl-3-(1,2,3,4-tetrahydro-1,4a,9b-trimethyl-1,4-methanodibenzofur-8-yl)-2H-1-benzofuran-6-carboxylate.

A solution of methyl 4-iodo-3-(1,2,3,4-tetrahydro-1,4a,9b-trimethyl-1,4-methanodibenzofur-8-yl)-1-propenyloxybenzoate (0.71 g, 1.3 mmol), palladium diacetate (0.03 g, 0.13 mmol), formic acid (0.06 ml, 1.6 mmol) and tributylamine (0.6 ml, 2.6 mmol) in 10 ml of acetonitrile is heated at 80° C. for 6 h. The reaction medium is concentrated on a rotary evaporator under vacuum at 40° C. 20 ml of water and 20 ml of ethyl ether are added. After separation of the phases by settling, the organic phase is washed twice with 20 ml of water, dried over magnesium sulphate and concentrated on a rotary evaporator under vacuum at 40° C. A mixture of the two diastereoisomers is obtained in a proportion of 50/50. The mixture of the two diastereoisomers is purified by flash chromatography on a column of silica (80% $CH_2Cl_2$, 20% heptane).

Colourless oil. Mass: 465 mg. Yield: 85%. $^1$H NMR ($CDCl_3$, 250 MHz): 0.76 to 1.63 (16H, m), 1.71 (3H, s), 2.21 (1H, d, J=4.3 Hz), 3.91 (3H, s), 4.48 (1H, d, J=8.5 Hz), 4.58 (1H, d, J=8.5 Hz) and 4.56 (1H, d, J=8.5 Hz): 2 diastereoisomers, 6.65 (1H Ar, d, J=8.3 Hz, 6.84 (1H Ar, d, J=2 Hz) and 6.87 (1H Ar, d, J=2 Hz): 2 diastereoisomers, 6.99 to 7.05 (2H Ar, m), 7.51 (1H Ar, s), 7.62 (2H Ar, d, J=7.8 Hz). $^{13}$C NMR ($CDCl_3$, 250 MHz): 17.87 to 17.98: 2 diastereoisomers, 19.47, 21.92, 23.54, 26.49, 34.08 and 34.12: 2 diastereoisomers, 42.12 and 42.15: 2 diastereoisomers, 49.23, 49.57 and 49.65: 2 diastereoisomers, 50.87, 52.11, 55.73 and 55.76: 2 diastereoisomers, 86.82 and 86.86: 2 diastereoisomers, 97.93, 108.53 and 108.61: 2 diastereoisomers, 110.84, 121.41 and 121.65: 2 diastereoisomers, 122.92, 123.69 and 123.73: 2 diastereoisomers, 126.38 and 126.43: 2 diastereoisomers, 130.52, 134.05, 136.63 and 136.71: 2 diastereoisomers, 141.86 and 141.93: 2 diastereoisomers, 157.57, 159.66 and 159.70: 2 diastereoisomers, 166.98.

Example 8

Process for the preparation of 3-methyl-3-(1,2,3,4-tetrahydro-1,4a,9b-trimethyl-1,4-methanodibenzofuran-8-yl)-2H-1-benzofuran-6-carboxylic acid A mixture of methyl 3-methyl-3-(1,2,3,4-tetrahydro-1,4a,9b-trimethyl-1,4-methanodibenzofur-8-yl)-2H-1-benzofuran-6-carboxylate (0.41 g, 0.98 mmol), sodium hydroxide (0.1 g, 2.5 mmol), lithium hydroxide (0.1 g, 2.5 mmol), methanol and water in THF is stirred for 48 h at room temperature.

The reaction medium is concentrated on a rotary evaporator under vacuum at 40° C., after which 10 ml of water are added. The suspension is acidified with concentrated hydrochloric acid solution to a pH of 1. The solid obtained is filtered off and is recrystallized from a heptane/ether mixture (1/5).

White solid. Mass: 311 mg. Yield: 78%. m.p.: 184° C.; $^1$H NMR (CDCl$_3$, 250 MHz): 0.78 to 1.63 (16H, m), 1.73 (3H, s), 2.21 (1H, d, J=3.8 Hz), 4.51 (1H, d, J=8.5 Hz), 4.59 (1H, d, J=8.5 Hz) and 4.61 (1H, d, J=8.5 Hz): 2 diastereoisomers, 6.67 (1H Ar, d, J=8.3 Hz), 6.86 (1H Ar, d, J=2 Hz) and 6.89 (1H Ar, d, J=2 Hz): 2 diastereoisomers, 7.02 to 7.08 (2H Ar, m), 7.59 (1H Ar, s), 7.70 (2H Ar, d, J=7.8 Hz). $^{13}$C NMR (CDCl$_3$, 250 MHz): 17.90 to 18.02: 2 diastereoisomers, 19.51, 21.94, 23.58, 26.48, 34.11, 42.15, 49.27, 49.65 and 49.73: 2 diastereoisomers, 50.91, 55.77, 86.88, 98.00, 108.61 and 108.70: 2 diastereoisomers, 111.40, 121.44 and 121.69: 2 diastereoisomers, 123.68 and 123.85: 2 diastereoisomers, 126.42 and 126.49: 2 diastereoisomers, 129.67, 134.14, 136.53 and 136.60: 2 diastereoisomers, 142.99 and 143.07: 2 diastereoisomers, 157.64, 159.74 and 159.78: 2 diastereoisomers, 171.94.

Example 9

Process for the preparation of methyl 3-allyl-3-(5,6,7,8-tetrahydro-5,5,8,8-tetramethyl-2-naphthyl)-2H-1-benzofuran-6-carboxylate A mixture of palladium bis(triphenylphosphine)diacetate (0.15 g, 0.2 mmol), tributylvinyltin (0.56 ml, 1.92 mmol) and methyl 4-iodo-3-[2-[5,6,7,8-tetrahydro-5,5,8,8-tetramethyl-2-naphthyl]-1-propenyloxy]benzoate (1 g, 1.99 mmol) in acetonitrile (20 ml) is heated at 80° C. for 3 days, adding tributylvinyltin (0.28 ml, 0.96 mmol) every 24 h. The reaction medium is concentrated on a rotary evaporator under vacuum at 40° C. 40 ml of water and 40 ml of ethyl ether are added. After separation of the phases by settling, the organic phase is washed twice with 40 ml of water, dried over magnesium sulphate and concentrated on a rotary evaporator under vacuum at 40° C.

The product is purified by flash chromatography on a column of silica (80% CH$_2$Cl$_2$, 20% heptane).

Colourless oil. Mass: 250 mg. Yield: 32%. $^1$H NMR (CDCl$_3$, 250 MHz): 1.13 (6H, s) 1.16 (6H, s), 1.57 (4H, s), 2.77 (2H, t, J=7 Hz), 3.79 (3H, s), 4.49 (1H, d, J=9 Hz), 4.55 (1H, d, J=9 Hz), 4.91 (1H, s), 4.97 (1H, d, J=6.5 Hz), 5.49 (1H, m), 6.92 (1H, dd, J=2 Hz, J=8.25 Hz), 7.05 (1H Ar, d, J=8.00 Hz), 7.07 to 7.14 (2H Ar, m), 7.41 (1H Ar, s), 7.54 (1H Ar, d, J=8.00 Hz). $^{13}$C NMR (CDCl$_3$, 250 MHz): 31.64, 31.76, 33.82, 34.24, 34.88, 34.97, 43.26, 51.93, 53.30, 83.69, 110.63, 118.78, 122.27, 123.84, 124.53, 124.82, 126.58, 130.58, 133.46, 138.42, 140.85, 143.21, 144.79, 160.24, 166.78.

Example 10

Process for the preparation of 3-allyl-3-(5,6,7,8-tetrahydro-5,5,8,8-tetramethyl-2-naphthyl)-2H-1-benzofuran-6-carboxylic acid A mixture of methyl 3-allyl-3-(5,6,7,8-tetrahydro-5,5,8,8-tetramethyl-2-naphthyl)-2H-1-benzofuran-6-carboxylate (240 mg, 0.61 mmol), sodium hydroxide (0.12 g, 3 mmol) and lithium hydroxide (0.06 g, 3 mmol) is stirred at room temperature for 3 days. The mixture is concentrated on a rotary evaporator under vacuum at 40° C. 10 ml of water and 10 ml of ethyl acetate are added. The mixture is acidified with concentrated hydrochloric acid solution to pH 1. After separation of the phases by settling, the organic phase is washed twice with 10 ml of water, dried over magnesium sulphate and concentrated on a rotary evaporator under vacuum at 40° C. The product is obtained by recrystallization from a heptane/ethyl ether mixture (3/1).

White solid. Mass: 128 mg. Yield: 54%, m.p.: 167° C.; $^1$H NMR (CDCl$_3$, 250 MHz): 1.23 (6H, s), 1.26 (6H, s), 1.67 (4H, s), 2.89 (2H, t, J=7 Hz), 4.61 (1H, d, J=8.75 Hz), 4.67 (1H, d, J=8.75 Hz), 5.04 (1H, s), 5.08 (1H, d, J=4.5 Hz), 5.60 (1H, m), 7.01 (1H, dd, J=2 Hz, J=8.25 Hz), 7.17 to 77.22 (3H Ar, m), 7.57 (1H Ar, s), 7.71 (hH Ar, dd, J=3.3, J=8.00 Hz). $^{13}$C NMR (CDCl$_3$, 250 MHz): 32.05, 32.18, 34.27, 34.69, 35.29, 35.38, 43.63, 53.78, 84.18, 111.57, 119.31, 123.41, 124.26, 124.95, 125.37, 127.05, 130.05, 133.79, 139.97, 141.11, 143.74, 145.30, 160.69, 171.87.

Example 11

Process for the preparation of [3-(5,6,7,8-tetrahydro-5,5,8,8-tetramethyl-2-naphthyl)-3-methyl-2H-1-benzofur-5-oyl]-morpholine A solution of 3-(5,6,7,8-tetrahydro-5,5,8,8-tetramethyl-2-naphthyl)-3-methyl-2H-1-benzofuran-5-carboxylic acid (100 mg, 0.275 mmol), 1-hydroxybenzotriazole (74 mg, 0.55 mmol) 1,3-dicyclohexylcarbodiimide (112 mg, 0.55 mmol) and morpholine (0.024 ml, 0.255 mmol) in 5 ml of THF and 2 ml of DMF is stirred at room temperature for 6 hours. 30 ml of water and 30 ml of ethyl acetate are added. After stirring and separation of the phases by settling, the aqueous phase is extracted with 2×30 ml of ethyl acetate. The organic phases are then combined and washed twice with 30 ml of water and then dried over magnesium sulphate and concentrated on a rotary evaporator under vacuum at 40° C. The product is then purified by flash chromatography on a column of silica (50% heptane/50% ethyl acetate).

White solid. Mass: 80 mg. Yield: 70%. m.p.: 57° C.; $^1$H NMR (CDCl$_3$, 250 MHz): 1.18 (3H, s); 1.22 (3H, s); 1.26 (6H, s); 1.66 (4H, s); 1.73 (3H, s); 3.64 (8H, m); 4.52 (1H, d, J=9 Hz); 4.68 (1H, d, J=9 Hz); 6.87 (1H, d, J=8.25 Hz); 7.00 (1H, d, J=8.0 Hz); 7.11 to 7.29 (4H, m); $^{13}$C NMR (CDCl$_3$, 250 MHz): 26.03; 31.46; 31.57; 33.64; 34.03; 34.67; 34.77; 49.24; 66.56; 86.38; 109.37; 123.37; 123.64; 123.93; 126.30; 127.41; 128.05; 136.13; 142.01; 143.00; 144.48; 160.83; 170.37.

Example 12

Process for the preparation of N-4-hydroxyphenyl-3-(5,6,7,8-tetrahydro-5,5,8,8-tetramethyl-2-naphthyl)-3-methyl-2H-1-benzofuran-5-carboxamide A solution of 3-(5,6,7,8-tetrahydro-5,5,8,8-tetramethyl-2-naphthyl)-3-methyl-2H-1-benzofuran-5-carboxylic acid (100 mg, 0.275 mmol), 1-hydroxybenzotriazole (74 mg, 0.55 mmol), 1,3-dicyclohexylcarbodiimide (112 mg, 0.55 mmol) and 4-aminophenol (30 mg, 0.255 mmol) in 5 ml of THF and 2 ml of DMF is stirred at room temperature for 6 hours. 30 ml of water and 30 ml of ethyl acetate are added. After stirring and separation of the phases by settling, the aqueous phase is extracted with 2×30 ml of ethyl acetate. The organic phases are then combined and washed twice with 30 ml of water and then dried over magnesium sulphate, and concentrated on a rotary evaporator under vacuum at 40° C. The product is then purified by flash chromatography on a column of silica (50% heptane/50% ethyl acetate).

White solid. Mass: 45 mg. Yield: 36%. m.p.: 50° C.; $^1$H NMR (CDCl$_3$, 250 MHz): 1.21 (3H, s); 1.25 (9H, s); 1.66 (4H, s); 1.74 (3H, s); 4.52 (1H, a, J=9 Hz); 4.68 (1H, d, J=9 Hz); 6.70 (2H, d, J=8. 5 Hz); 6.90 (2H, d, J=8.5 Hz); 6.97 (1H, dd, J=8.75, 2.0); 7.20 to 7.27 (2H, m); 7.55 (1H, d, J=2.0 Hz); 7.72 (2H, m); $^{13}$C NMR (CDCl$_3$, 250 MHz): 26.2; 31.7; 31.9; 33.9; 34.3; 34.9; 35.0; 49.3; 87.0; 109.8; 115.9; 123.3; 123.6; 123.8; 126.7; 127.4; 128.4; 129.8; 136.7; 142.2; 143.3; 144.9; 153.7; 162.8; 166.2

Example 13

Process for the preparation of N-butyl-3-methyl-3-(5,5,8,8-tetramethyl-5,6,7,8-tetrahydronaphth-2-yl)-2H-1-benzofuran-5-carboxamide A solution of 3-(5,6,7,8-tetrahydro-5,5,8,8-tetramethyl-2-naphthyl)-3-methyl-2H-1-benzofuran-5-carboxylic acid (100 mg, 0.275 mmol), 1-hydroxybenzotriazole (74 mg, 0.55 mmol), 1,3-dicyclohexylcarbodiimide (112 mg, 0.55 mmol) and butylamine (19 mg, 0.255 mmol) in 5 ml of THF and 2 ml of DMF is stirred at room temperature for 6 hours. 30 ml of water and 30 ml of ethyl acetate are added. After stirring and separation of the phases by settling, the aqueous phase is extracted with 2×30 ml of ethyl acetate. The organic phases are then combined and washed twice with 30 ml of water, then dried over magnesium sulphate and concentrated on a rotary evaporator under vacuum at 40° C. The product is then purified by flash chromatography on a column of silica (50% heptane/50% ethyl acetate).

Light oil. Mass: 80 mg. Yield: 69%. $^1$H NMR (CDCl$_3$, 250 MHz): 0.93 (3H, t); 1.24 (3H, s); 1.25 (6H, s); 1.36 (2H, m); 1.39 (2H, m); 1.62 (4H, s); 1.78 (3H, s); 3.40 (2H, q, J=7.5 Hz, 13.0 Hz); 4.48 (1H, d, J=9.0 Hz); 4.65 (1H, d, J=9.0 Hz); 6.65 (1H, d, J=8.4 Hz); 6.97 (1H, dd, J=8.75 Hz, 2.0 Hz); 7.22 (2H, m); 7.48 (1H, d, J=2.0 Hz); 7.62 (1H, dd, J=8.75 Hz, 2.0 Hz); $^{13}$C NMR (CDCl$_3$, 250 MHz): 13.7; 20.1; 26.2; 31.68; 31.74; 33.8; 34.3; 34.8; 34.9; 39.7; 49.3; 86.9; 109.4; 123.4; 123.8; 124.0; 126.6; 127.7; 136.5; 142.3; 143.2; 144.7; 162.2; 167.1

Example 14

Process for the preparation of methyl 3-[4-(1-adamantyl)-3-methoxyphenyl-3-methyl-2H-1-benzofuran]-6-carboxylate Methyl 3-[4-(1-adamantyl)-3-methoxybenzoylmethyloxy]-4-iodobenzoate A solution of 4-(1-adamantyl)-3-methoxy-2'-bromoacetophenone (860 mg, 2.37 mmol), methyl 3-hydroxy-4-iodobenzoate (660 mg, 2.37 mmol) and potassium carbonate (330 mg, 2.39 mmol) in methyl ethyl ketone (20 ml) is refluxed for five hours. The reaction medium is filtered and 30 ml of water and 30 ml of ethyl ether are then added. After stirring and separation of the phases by settling, the organic phase is washed twice with 30 ml of water, dried over magnesium sulphate and concentrated on a rotary evaporator under vacuum at 40° C. The product is purified by flash chromatography on a column of silica (CH$_2$Cl$_2$).

White solid. Mass: 900 mg. Yield: 68%. m.p.: 136° C.; $^1$H NMR (CDCl$_3$, 250 MHz): 1.78 (6H, s), 2.11 (9H, s), 3.89 (3H, s), 3.90 (3H, s), 5.42 (2H, s), 7.32 to 7.42 (3H Ar, m), 7.43 (1H Ar, s, J=1.5 Hz), 7.48 (1H Ar, dd, J=8 Hz, J=1.5 Hz), 7.82 (1H Ar, d, J=8 Hz). $^{13}$C NMR (CDCl$_3$, 250 MHz): 28.97; 37.03; 37.76; 40.24; 40.32; 52.42; 55.21; 71.62; 93.26; 110.35; 112.61; 120.91; 124.15; 126.91; 131.65; 132.98; 139.94; 145.59; 157.13; 159.34; 166.39; 192.69.

Methyl 4-iodo-3-[2-[4-(1-adamantyl)-3-methoxyphenyl]-1-propenyloxy]benzoate

A solution of 30% sodium methoxide in methanol (0.3 ml, 1.6 mmol) is added over 8 hours to a mixture of methyl 3-[4-(1-adamantyl)-3-methoxybenzoylmethyloxy]-4-iodobenzoate (870 mg, 1.55 mmol) and methyltriphenylphosphine bromide (790 mg, 2.21 mmol) in THF (10 ml).

The mixture is stirred at room temperature for 12 hours. The mixture is concentrated on a rotary evaporator under vacuum at 40° C. It is extracted with 40 ml of ethyl ether and 40 ml of water. After separation of the phases by settling, the organic phase is washed twice with 40 ml of water, dried over anhydrous magnesium sulphate and concentrated on a rotary evaporator under vacuum at 40° C. The product is purified by flash chromatography on a column of silica (60% CH$_2$Cl$_2$, 40% heptane).

White solid. Mass: 535 mg. Yield: 60%. m.p.: 109–111° C.; $^1$H NMR (CDCl$_3$, 250 MHz): 1.77 (6H, s); 2.09 (3H, s); 2.10 (6H, s); 3.86 (3H, s); 3.91 (3H, s); 4.98 (2H s); 5.62 (2H s); 7.00 to 7.04 (2H Ar, m); 7.21 (1H Ar, d, J=7.25 Hz), 7.38 (1H Ar, dd, J=1.75 Hz, J=8.25 Hz), 7.50 (1H Ar, d, J=1.75 Hz), 7.87 (1H Ar, d, J=8 Hz). $^{13}$C NMR (CDCl$_3$, 250 MHz): 14.53; 23.11; 29.44; 29.51; 32.30; 37.35; 37.54; 41.00; 52.76; 55.55; 71.29; 93.70; 110.22; 113.12; 114.87; 118.66; 123.98; 126.97; 131.98; 137.35; 139.13; 140.03; 142.52; 157.69; 159.28; 166.93

Methyl 3-[4-(1-adamantyl)-3-methoxyphenyl-3-methyl-2H-1-benzofuran]-6-carboxylate A mixture of tributylamine (0.44 ml, 1.84 mmol), sodium formate (70 mg, 1.01 mmol), palladium diacetate (20 mg, 0.092 mmol), 15-crown-5 (100 μl, 5 μ mol) and methyl 4-iodo-3-[2-[4-(1-adamantyl)-3-methoxyphenyl]-1-prepenyloxy]benzoate (515 mg, 0.92 mmol) in acetonitrile (10 ml). Formic acid (0.035 ml, 0.92 mmol) is added after heating for 3 h. The reaction medium is concentrated on a rotary evaporator under vacuum at 40° C.

5 ml of water and 5 ml of ethyl acetate are added. After separation of the phases by settling, the organic phase is washed twice with 5 ml of water, dried over magnesium sulphate and concentrated on a rotary evaporator under vacuum at 40° C.

The product is purified by flash chromatography on a column of silica (70% CH$_2$Cl$_2$, 30% heptane).

White solid. Mass: 362 mg. Yield: 91%. m.p.: 108–111° C.; $^1$H NMR (CDCl$_3$, 250 MHz): 1.67 (9H, s), 1.98 (9H, s), 3.65 (3H, s), 3.83 (3H, s), 4.41 (1H, d, J=8.75 Hz), 4.57 (1H, d, J=8.75 Hz), 6.62 (1H Ar, d, J=1.75 Hz), 6.75 (1H Ar, dd, J=8.25 Hz, J=1.75 Hz), 7.02 (1H Ar, d, J=7.75 Hz), 7.07 (1H Ar, d, J=7.75 Hz), 7.44 (1H Ar, s), 7.55 (1H Ar, d, J=8 Hz). $^{13}$C NMR (CDCl$_3$, 250 MHz): 26.04, 29.10, 36.76, 37.15, 40.62, 49.79, 52.15, 54.98, 86.49, 110.17, 110.92, 118.24, 122.93, 123.96, 126.50, 130.72, 137.20, 141.20, 144.07, 158.88, 159.82, 166.97.

Example 15

Process for the preparation of 3-[4-(1-adamantyl)-3-methoxyphenyl-3-methyl-2H-1-benzofuran]-6-carboxylic acid A mixture of methyl 3-[4-(1-adamantyl)-3-methoxyphenyl-3-methyl-2H-1-benzofuran]-6-carboxylate (320 mg, 0.74 mmol), sodium hydroxide (160 mg, 4 mmol), lithium hydroxide (160 mg, 4 mmol), methanol (1 ml) and water (1 ml) in THF (6 ml) is stirred at room temperature for 3 days. The mixture is concentrated on a rotary evaporator under vacuum at 40° C. 10 ml of water and 10 ml of ethyl ether are added. The mixture is acidified with concentrated hydrochloric acid solution to pH=1. After separation of the phases by settling, the organic phase is washed twice with 10 ml of water, dried over magnesium sulphate and concentrated on a rotary evaporator under vacuum at 40° C.

White solid. Mass: 282 mg. Yield: 91%. m.p.: 217–222° C.; $^1$H NMR (CDCl$_3$, 250 MHz): 1.76 (9H, s), 2.06 (9H, s), 3.74 (3H, s), 4.51 (1H, d, J=8.75 Hz), 4.67 (1H, d, J=8.75 Hz), 6.71 (1H Ar, s) 6.85 (1H Ar, d, J=8 Hz), 7.09 to 7.17 (2H Ar, m), 7.59 (1H Ar, s), 7.71 (1H Ar, d, J=7.75 Hz). $^{13}$C NMR (CDCl$_3$, 250 MHz): 25.86, 28.85, 36.50, 36.92, 40.39, 49.54, 54.79, 86.16, 109.94, 110.88, 118.03, 122.92, 123.63, 126.24, 131.34, 136.85, 140.62, 143.99, 158.63, 159.52, 168.28.

Example 16

Process for the preparation of methyl 3-(3-methyl-5,6,7,8-tetrahydro-5,5,8,8-tetramethyl-2-naphthyl)-3-methyl-2H-1-benzofuran-6-carboxylate 3-methyl-5,6,7,8-tetrahydro-5,5,8,8-tetramethyl-2'-bromoacetonaphthone A solution of bromine (0.6 ml, 11.7 mmol) in dichloromethane (5 ml) is added dropwise to a solution of 3-methyl-5,6,7,8-tetrahydro-5,5,8,8-tetramethyl-2-acetonaphthone (2.59 g, 10.6 mmol) in dioxane (15 ml) and ethyl ether (15 ml). The solution is stirred for 1 h at room temperature and is then poured on to a mixture of ice-water (25 g) and ethyl ether (25 ml). After separation of the phases by settling, the organic phase is washed twice with water (25 ml), dried over anhydrous magnesium sulphate and concentrated on a rotary evaporator under vacuum at 40° C. The product is purified by flash chromatography on a column of silica (50% CH$_2$Cl$_2$, 50% heptane) (Rf: 0.3).

White solid. Mass: 1.2 g. Yield: 35%. m.p.: oil; $^1$H NMR (CDCl$_3$, 250 MHz): 1.29 (6H, s), 1.30 (6H, s), 1.70 (4H, s), 2.49 (1H, s), 4.59 (3H, s), 7.18 (1H Ar, s), 7.67 (1H Ar, s).

Methyl 3-[(3-methyl-5,6,7,8-tetrahydro-5,5,8,8-tetramethyl-2-naphthoyl)methyloxy]-4-iodobenzoate.

A solution of 3-methyl-5,6,7,8-tetrahydro-5,5,8,8-tetramethyl-2'-bromoacetonaphthone (1.20 g, 3.7 mmol), methyl 3-hydroxy-4-iodobenzoate (1.15 g, 4.1 mmol) and potassium carbonate (0.56 g, 4 mmol) in methyl ethyl ketone (25 ml) is refluxed for three hours. The reaction medium is filtered and then concentrated on a rotary evaporator. 40 ml of water and 40 ml of ethyl acetate are added. After stirring and separation of the phases by settling, the organic phase is washed twice with 40 ml of water, dried over magnesium sulphate and concentrated on a rotary evaporator under vacuum at 40° C. The product is purified by flash chromatography on a column of silica (80% CH$_2$Cl$_2$, 20% heptane), (Rf: 0.4).

White solid. Mass: 1.65 g. Yield: 86%. m.p.: 89–94° C.; $^1$H NMR (CDCl$_3$, 250 MHz): 1.29 (6H, s), 1.31 (6H, s), 1.70 (4H, s), 2.49 (3H, s), 3.88 (3H, s), 5.30 (2H, s), 7.19 (1H Ar, s), 7.30 (1H Ar, s), 7.37 (1H Ar, d, J=8 Hz), 7.63 (1H Ar, s), 7.87 (1H Ar, d, J=8 Hz). $^{13}$C NMR (CDCl$_3$, 250 MHz): 20.94, 31.49, 31.87, 33.97, 34.46, 34.77, 34.83, 52.31, 72.54, 92.94, 112.36, 123.93, 126.99, 130.40, 131.49, 132.15, 139.83, 142.55, 149.94, 156.98, 166.27, 196.63.

Methyl 4-iodo-3-[2-(3-methyl-5,6,7,8-tetrahydro-5,5,8,8-tetramethyl-2-naphthyl)-1-propenyloxy]benzoate Sodium methoxide (0.62 ml, 3.17 mmol) is added over 8 hours to a mixture of methyl 3-(3-methyl-5,6,7,8-tetrahydro-5,5,8,8-tetramethyl-2-naphthoyl-methyloxy)-4-iodobenzoate (1.6 g, 3.1 mmol) and methyltriphenylphosphine bromide (1.51 g, 4.2 mmol) in THF (15 ml).

The mixture is stirred for 3 days at room temperature. The mixture is concentrated on a rotary evaporator under vacuum at 40° C. It is extracted with 30 ml of ethyl ether and 30 ml of water. After separation of the phases by settling, the organic phase is washed twice with 30 ml of water, dried over anhydrous magnesium sulphate and concentrated on a rotary evaporator under vacuum at 40° C. The product is purified by flash chromatography on a column of silica (90% CH$_2$Cl$_2$, 10% heptane) (Rf: 0.67).

White solid. Mass: 0.54 g. Yield: 34%. m.p.: 83–86° C.; $^1$H NMR (CDCl$_3$, 250 MHz): 1.27 (6H, s), 1.29 (6H, s), 1.68 (4H, s), 2.32 (3H, s), 3.89 (3H, s), 4.76 (2H, s), 5.22 (1H, s), 5.77 (1H, s), 7.13 (1H Ar, d, J=6.75 Hz), 7.36 to 7.43 (2H Ar, m), 7.87 (1H Ar, d, J=8.00). $^{13}$C NMR (CDCl$_3$, 250 MHz): 31.91, 31.99, 33.97, 34.06, 35.22, 52.37, 71.51, 93.14, 112.58, 115.53, 123.50, 127.03, 128.26, 131.57, 132.49, 136.36, 139.62, 142.37, 143.71, 144.46, 157.19, 166.54.

Methyl 3-(3-methyl-5,6,7,8-tetrahydro-5,5,8,8-tetramethyl-2-naphthyl)-3-methyl-2H-1-benzofuran-6-carboxylate A mixture of tributylamine (0.4 ml, 0.88 mmol), palladium diacetate (0.017 g, 0.083 mmol), formic acid (0.034 ml, 0.91 mmol), sodium formate (60 mg, 0.88 mmol), 15-crown-5 and methyl 4-iodo-3-[2-(3-methyl-5,6,7,8-tetrahydro-5,5,8,8-tetramethyl-2-naphthyl)-1-propenyloxy] benzoate (429 mg, 0.83 mmol) in acetonitrile (10 ml) is heated at 45° C. for 8 h. The reaction medium is concentrated on a rotary evaporator under vacuum at 40° C. 20 ml of water and 20 ml of ethyl ether are added. After separation of the phases by settling, the organic phase is washed twice with 20 ml of water, dried over magnesium sulphate and concentrated on a rotary evaporator under vacuum at 40° C.

The product is purified by flash chromatography on a column of silica (90% CH$_2$Cl$_2$/10% heptane) (Rf: 0.38).

White solid. Mass: 180 mg. Yield: 55%. m.p.: 174.6° C.; $^1$H NMR (CDCl$_3$, 250 MHz): 1.21 (3H, s), 1.26 (9H, s), 1.67 (4H, s), 1.76 (3H, s), 1.97 (3H, s), 4.49 (1H, d, J=9 Hz), 4.78 (1H, d, J=9 Hz), 7.03 to 7.05 (2H Ar, m), 7.28 (1H Ar, s), 7.48 (1H Ar, s), 7.61 (1H Ar, d, J=7.75 Hz). $^{13}$C NMR (CDCl$_3$, 250 MHz): 21.63; 29.52; 32.03; 32.13; 32.26; 32.38; 34.14; 34.48; 35.54; 35.61; 50.35; 52.51; 85.05; 110.95; 122.94; 124.27; 125.60; 130.87; 131.13; 133.71; 139.10; 142.00; 142.28; 144.06; 160.03; 167.44.

Example 17

Process for the preparation of 3-(3-methyl-5,6,7,8-tetrahydro-5,5,8,8-tetramethyl-2-naphthyl)-3-methyl-2H-1-benzofuran-6-carboxylic acid A mixture of methyl 3-(3-methyl-5,6,7,8-tetrahydro-5,5,8,8-tetramethyl-2-naphthyl)-3-methyl-2H-1-benzofuran-6-carboxylate (140 mg, 0.36 mmol), sodium hydroxide (0.06 g, 1.54 mmol) and lithium hydroxide (0.06 g, 1.54 mmol) is stirred at room temperature for 24 h. The mixture is concentrated on a rotary evaporator under vacuum at 40° C. 10 ml of water and 10 ml of ethyl ether are added. The mixture is acidified with concentrated hydrochloric acid solution to pH 1. After separation of the phases by settling, the organic phase is washed twice with 10 ml of water, dried over magnesium sulphate and concentrated on a rotary evaporator under vacuum at 40° C. The product is obtained by recrystallization from a heptane/ethyl ether mixture (3/1). (90 EtOAc, 10 heptane) (Rf: 0.56).

White solid. Mass: 118 mg. Yield: 87%. m.p.: 247° C.; $^1$H NMR (CDCl$_3$, 250 MHz): 1.20 (3H, s), 1.25 (9H, s), 1.66 (4H, s), 1.76 (3H, s), 1.98 (3H, s), 4.49 (1H, d, J=9 Hz), 4.77 (1H, d, J=9 Hz), 7.02 to 7.05 (2H Ar, m), 7.27 (1H Ar, s), 7.50 (1H Ar, s), 7.63 (1H Ar, d, J=7.15 Hz). $^{13}$C NMR (CDCl$_3$, 250 MHz): 21.60; 29.48; 32.00; 32.10; 32.22; 32.35; 34.09; 34.43; 35.51; 35.57; 50.30; 84.94; 111.14; 123.16; 124.14; 125.57; 131.06; 313.56; 133.66; 139.17; 141.69; 142.20; 143.95; 159.92; 169.11.

Example 18

Process for the Preparation of methyl 3-(5,6,7,8-tetrahydro-5,5,8,8-tetramethyl-2-naphthyl)-3-(3,5-di-tert-butyl-4-hydroxybenzyl)-2H-1-benzofuran-6-carboxylate Tris[3,5-bis(1,1-dimethylethyl)-4-(trimethylsilyloxy)-phenyl]boroxine.

A 2.5 M solution of BuLi in hexane (4.7 ml, 11.8 mmol) is added dropwise to a suspension of 4-bromo-2,6-tert-butyl trimethylsilyloxyphenyl (4 g, 11.2 mmol) in TMEDA/THF (5 ml/40 ml) at −78° C. Stirring is continued for 1 h at the same temperature, after which trimethyl borate is added dropwise at −78° C. Stirring is continued for 45 min at −78° C. and 50 ml of saturated NH$_4$Cl solution are added. The mixture is allowed to return to room temperature. The pH of the solution is adjusted to 6.5 with concentrated HCl solution. The mixture is extracted with CH$_2$Cl$_2$, washed twice with water, dried and concentrated on a rotary evaporator under vacuum. The product is crystallized from heptane.

Yellow powder. Mass: 2.36 g. Yield: 66%. m.p.=230° C. (235–237° C.)$^{129}$; NMR δ ppm: $^1$H (250 MHz, CDCl$_3$): 0.46 (9H, s), 1.47 (18H, s), 8.16 (2H, s).

Methyl 3-(5,6,7,8-tetrahydro-5,5,8,8-tetramethyl-2-naphthyl)-3-(3,5-di-tert-butyl-4-hydroxybenzyl)-2H-1-benzofuran-6-carboxylate A mixture of palladium diacetate (9 mg, 0.04 mmol), methyl 4-iodo-3-[2-(5,6,7,8-tetrahydro-5,5,8,8-tetramethyl-2-naphthyl)-1-propenyloxy]benzoate (180 mg, 0.2 mmol), a solution containing 30% sodium methoxide in methanol (70 mg, 0.4 mmol) and the product tris[3,5-bis(1,1-dimethylethyl)-4-(trimethylsilyloxy)-phenyl]boroxine (100 mg, 0.2 mmol) in DME (3 ml) is heated at 60° C. for 2 h. The reaction medium is concentrated on a rotary evaporator under vacuum at 40° C. and is treated with 10 ml of water and ethyl ether. After separation of the phases by settling, the organic phase is washed twice with 10 ml of water, dried over magnesium sulphate and concentrated on a rotary evaporator under vacuum at 40° C. The product is purified by flash chromatography on a column of silica (40% CH$_2$Cl$_2$, 60% heptane).

Amorphous yellow product. Mass: 22 mg. Yield: 19%. NMR δ ppm: $^1$H (250 MHz, CDCl$_3$): 1.20 to 1.27 (30H, m, CH$_3$ TTN and tBu), 1.67 (4H, s, CH$_2$ TTN), 3.10 (1H, d, J=13 Hz, H of the CH$_2$ of the BHT), 3.40 (1H, d, J=13 Hz, H of the CH$_2$ of the BHT), 3.90 (3H, s, O—CH$_3$), 4.60 (1H, d, J=9 Hz, H of the O—CH$_2$), 4.92 (1H, d, J=9 Hz, H of the O—CH$_2$), 5.03 (1H, s, OH), 6.39 (2H Ar, s), 6.74 (1H Ar, d, J=8 Hz), 7.04 (1H Ar, dd, J=2 Hz, J=8.3 Hz), 7.23 to 7.27 (2H Ar, m), 7.42 (1H Ar, d, J=1.5 Hz), 7.54 (1H Ar, dd, J=1.5 Hz, J=8 Hz). $^{13}$C (250 MHz, CDCl$_3$): 30.19 (CH$_3$ tBu), 31.78 (CH$_3$ TTN), 31.86 (CH$_3$ TTN), 32.05 (CH$_3$ TTN), 33.96 (C tBu), 34.04 (C TTN), 34.39 (C TTN), 35.02 (CH$_2$ TTN), 35.10 (CH$_2$ TTN), 46.72 (CH$_2$), 52.10 (C), 55.39 (OCH$_3$), 83.49 (CH$_2$O), 111.77 (CH Ar), 121.53 (CH Ar), 124.32 (CH Ar), 124.96 (CH Ar), 126.51 (CH Ar), 126.60 (CH Ar), 126.94 (CH Ar), 127.08 (C Ar), 130.51 (C Ar), 134.86 (C Ar), 137.13 (C Ar), 140.47 (C Ar), 143.21 (C Ar), 145.02 (C Ar), 152.46 (C—O Ar), 160.53 (C—O Ar), 167.01 (COO).

Example 19

Process for the preparation of 3-(5,6,7,8-tetrahydro-5,5,8,8-tetramethyl-2-naphthyl)-3-(3,5-di-tert-butyl-4-hydroxybenzyl)-2H-1-benzofuran-6-carboxylic acid A solution of the above product and sodium thiomethoxide (4 equivalents) in DMF is heated at 100° C. for 4 h. Water and ethyl ether are added. The mixture is acidified to pH=1 with concentrated hydrochloric acid solution. The organic phase is washed twice with water, dried over anhydrous magnesium sulphate and concentrated on a rotary evaporator under vacuum at 40° C.

White powder. Mass: 71 mg. Yield: 83%. m.p.=211–213° C. C$_{38}$H$_{48}$O$_4$ Mw: 568.80; Elemental analysis: Calculated: C: 80.24, H: 8.51. Found: C: 80.00, H: 8.62. MS m/z: 567 (M+). IR (cm$^{-1}$): 1293 =C—O, 1436 C=C, 1688 C=O, 2959 C—H. NMR δ ppm: $^1$H (250 MHz, CDCl$_3$): 1.21 to 1.27 (30H, m, CH$_3$ TTN and tBu), 1.68 (4H, 8, CH$_2$ TTN), 3.12 (1H, d, J=13 Hz, H of the CH$_2$ of the BHT), 3.42 (1H, d, J=13 Hz, H of the CH$_2$ of the BHT), 4.61 (1H, d, J=9 Hz, H of the O—CH$_2$), 4.77 (1H, d, J=9 Hz, H of the O—CH$_2$), 5.01 (1H, s, OH), 6.39 (2H Ar, s), 6.76 (1H Ar, d, J=8 Hz), 7.06 (1H Ar, d, J=8 Hz), 7.24 to 7.28 (2H Ar, m), 7.49 (1H Ar, s), 7.61 (1H Ar, d, J=8 Hz), 12.85 (1H, COOH). $^{13}$C (250 MHz, CDCl$_3$): 30.24 (CH$_3$ tBu), 31.86 (CH$_3$ TTN), 31.92 (CH$_3$ TTN), 32.10 (CH$_3$ TTN), 34.02 (C tBu), 34.10 (C TTN), 34.46 (C TTN), 35.08 (CH$_2$ TTN), 35.16 (CH$_2$ TTN), 46.72 (CH$_2$), 55.52 (C), 83.57 (CH$_2$O), 111.33 (CH Ar), 122.22 (CH Ar), 124.35 (CH Ar), 125.00 (CH Ar), 126.69 (CH Ar), 126.98 (CH Ar), 127.07 (C Ar), 129.55 (C Ar), 134.97 (C Ar), 138.27 (C Ar), 140.39 (C Ar), 143.34 (C Ar), 145.14 (C Ar), 152.55 (C—O Ar), 160.66 (C—O Ar), 171.08 (COO).

Example 20

Process for the preparation of 3-(5,6,7,8-tetrahydro-5,5,8,8-tetramethyl-2-naphthyl)-3-methyl-2H-1-benzofuran-5-methanol A 1M solution of borane in THF (7.7 ml, 7.7 mmol) is added dropwise at OOC to a solution of 3-methyl-3-(5,6,7,8-tetrahydro-5,5,8,8-tetramethyl-2-naphthyl)-2H-1-benzofuran-5-carboxylic acid (1.7 g, 4.7 mol) in THF (10 ml). The mixture is stirred for 4 h at room temperature and 2 ml of a solution of THF and water (1:1) is then added. After concentration on a rotary evaporator under vacuum at 40° C. The mixture is extracted with ethyl acetate. The organic phase is washed with water, dried over anhydrous magnesium sulphate, concentrated on a rotary evaporator under vacuum at 40° C. The product is purified by flash chromatography on a column of silica.

Amorphous yellow solid. Mass: 1.7 g. Yield: quantitative. C$_{24}$H$_{30}$O$_2$ Mw: 350.50; Calculated: C: 82.24, H: 8.63. Found: C: 82.40, H: 8.50. MS m/z: 349 (M+). NMR δ ppm: $^1$H (250 MHz, CDCl$_3$): 1.20 to 1.25 (12H, m), 1.66 (4H, s), 1.72 (3H, s), 3.47 (1H, s), 4.44 (1H, d, J=8.8 Hz), 4.59 (2H, s), 4.60 (1H, d, J=8.8 Hz), 6.84 (1H Ar, d, J=8 Hz), 7.01 (1H Ar, dd, J=8.3, J=2.3 Hz), 7.05 (1H Ar, d, J=1.8 Hz), 7.17 to 7.22 (3H Ar, m). $^{13}$C (250 MHz, CDCl$_3$): 25.86 (CH$_3$), 31.39 (CH$_3$ TTN), 31.48 (CH$_3$ TTN), 31.51 (CH$_3$ TTN), 33.55 (C TTN), 33.97 (C TTN), 34.65 (CH$_2$ TTN), 34.75 (CH$_2$ TTN), 49.25 (C), 65.05 (CH$_2$OH), 86.02 (CH$_2$O), 109.29 (CH Ar), 123.07 (CH Ar), 123.45 (CH Ar), 123.78 (CH Ar), 126.11 (CH Ar), 127.26 (CH Ar), 133.18 (C Ar), 135.93 (C Ar), 142.38 (C Ar), 142.65 (C Ar), 144.27 (C Ar), 159.00 (C—O Ar).

Example 21

Process for the preparation of 3-(5,6,7,8-tetrahydro-5,5,8,8-tetramethyl-2-naphthyl)-3-methyl-2H-1-benzofuran-5-carbaldehyde A mixture of the alcohol obtained above (1 g, 2.86 mmol) and pyridinium dichromate (2.15 g, 5.7 mmol) in dichloromethane is stirred at room temperature for 3 h. After filtration and concentration on a rotary evaporator under vacuum at 40° C., the product is purified by flash chromatography on a column of silica.

Oil. Mass: 0.98 g. Yield: 98%. $C_{24}H_{28}O_2$ Mw: 348.48. Elemental analysis: Calculated: C: 82.72, H: 8.10. Found: C: 82.50, H: 8.10. MS m/z: 349 (M+). NMR δ ppm: $^1$H (250 MHz, $CDCl_3$): 1.20 to 1.26 (12H, m), 1.67 (4H, s), 1.76 (3H, s), 4.57 (d, 1H, J=8.9), 4.73 (d, 1H, J=8.9), 6.96 (1H Ar, s), 7.00 (1H Ar, s), 7.20 to 7.25 (2H Ar, m), 7.59 (1H Ar, d, J=1.5 Hz), 7.74 (1H Ar, dd, J=8.3 Hz, J=1.8 Hz), 9.83 (1H, s). $^{13}$C (250 MHz, $CDCl_3$): 26.44 ($CH_3$), 31.77 ($CH_3$ TTN), 31.87 ($CH_3$ TTN), 31.91 ($CH_3$ TTN), 33.99 (C TTN), 34.39 (C TTN), 34.98 ($CH_2$ TTN), 35.09 ($CH_2$ TTN), 49.04 (C), 87.45 ($CH_2O$), 110.26 (CH Ar), 123.74 (CH Ar), 124.12 (CH Ar), 125.52 (CH Ar), 126.75 (CH Ar), 130.90 (C Ar), 132.95 (CH Ar), 137.68 (C Ar), 141.99 (C Ar), 143.48 (C Ar), 144.94 (C Ar), 155.10 (C—O Ar), 190.67 (CHO).

Example 22

Process for the preparation of methyl (−)-3-(5,6,7,8-tetrahydro-5,5,8,8-tetramethyl-2-naphthyl)-3-methyl-2H-1-benzofuran-5-carboxylate A mixture of calcium carbonate (100 mg, 1 mmol), palladium diacetate (10 mg, 0.05 mmol), sodium formate (68 mg, 1 mmol), methyl 3-iodo-4-[2-(5,6,7,8-tetrahydro-5,5,8,8-tetramethyl-2-naphthyl)-1-propenyloxy]benzoate (250 mg, 0.5 mmol), (R)-(+)-2,2'-bis-(diphenylphosphino)-1,1'-binaphthyl (65 mg, 0.1 mmol) and silver zeolite (Aldrich 36,660-9) in acetonitrile (7 ml) is heated at 60° C. for 2 days. The reaction medium is filtered through Celite and concentrated on a rotary evaporator under vacuum at 40° C. 10 ml of water and 10 ml of ethyl ether are added. After separation of the phases by settling, the organic phase is washed twice with 10 ml of water, dried over magnesium sulphate and concentrated on a rotary evaporator under vacuum at 40° C. The product is purified by flash chromatography on a column of silica.

White solid. Mass: 105 mg. Yield: 56%. $[\alpha]_d^{20}$ ($CHCl_3$): −151°. ee: 68.4%.

Example 23

Process for the preparation of methyl (+)-3-(5,6,7,8-tetrahydro-5,5,8,8-tetramethyl-2-naphthyl)-3-methyl-2H-1-benzofuran-5-carboxylate Same procedure as above with (S)-(−)-2,2'-bis (diphenylphosphino)-1,1'-binaphthyl.

White solid. Mass: 75 mg. Yield: 40%. $[\alpha]_d^{20}$ ($CHCl_3$): +116°. ee: 58.8%.

Example 24

Process for the preparation of methyl (−)-3-(5,6,7,8-tetrahydro-5,5,8,8-tetramethyl-2-naphthyl)-3-methyl-2H-1-benzofuran-6-carboxylate The experimental procedure is similar to that followed in order to obtain Example 22, applied to methyl 4-iodo-3-[2-(5,6,7,8-tetrahydro-5,5,8,8-tetramethyl-2-naphthyl)-1-propenyloxy]benzoate.

White solid. Mass: 75 mg. Yield: 40%. $[\alpha]_d^{20}$ ($CHCl_3$): −29.8°. ee: 79.6%.

Example 25

Process for the preparation of methyl (+)-3-(5,6,7,8-tetrahydro-5,5,8,8-tetramethyl-2-naphthyl)-3-methyl-2H-1-benzofuran-6-carboxylate The experimental procedure is similar to that followed in order to obtain Example 23, applied to methyl 4-iodo-3-[2-(5,6,7,8-tetrahydro-5,5,8,8-tetramethyl-2-naphthyl)-1-propenyloxy]benzoate.

White solid. Mass: 75 mg. Yield: 40%. $[\alpha]_d^{20}$ ($CHCl_3$): +28.5°. ee: 81%.

Example 26

Process for the Preparation of methyl 3-(5,6,7,8-tetrahydro-5,5,8,8-tetramethyl-2-naphthyl)-3-(2-hexenyl)-2H-1-benzofuran-6-carboxylate Methyl 4-iodo-3-[2-(5,6,7,8-tetrahydro-5,5,8,8-tetramethyl-2-naphthyl)-2-octenyloxy]benzoate.

The experimental procedure is similar to that followed in order to obtain methyl 4-iodo-3-[2-(5,6,7,8-tetrahydro-5,5,8,8-tetramethyl-2-naphthyl)-1-propenyloxy]benzoate, applied to methyl 3-[(5,6,7,8-tetrahydro-5,5,8,8-tetramethyl-2-naphthoyl)methyloxy]-4-iodobenzoate and hexyltriphenylphosphonium bromide.

White solid. Mass: 653 mg. Yield: 21%. m.p.=62° C. $C_{30}H_{39}IO_3$ Mw=574.54; Elemental analysis: Calculated: C: 62.72, H: 6.84. Found: C: 62.41, H: 6.72. MS m/z: 574 (M+); IR ($cm^{-1}$): 1210=C—O, 1490 C═C, 1718 C═O, 2956–2962 C—H. NMR δ ppm: $^1$H (250 MHz, $CDCl_3$): 0.82 to 0.88 (twice 3H, m) 1.29 to 1.42 (18H, m, $CH_3$ TTN and $CH_2$ 4.5 and 6), 1.67 (4H, s, $CH_2$ TTN), 2.03 (H No. 3 for the major product, d, J=7.5 Hz), 2.09 (H No. 3' for the major product, d, J=7.5 Hz), 2.28 (H No. 3 for the minor product, d, J=7.3 Hz), 2.33 (H No. 3' for the minor product, d, J=7.5 Hz), 3.89 (3H, s, for the major product), 3.91 (3H, s, for the minor product), 4.78 (2H, s, for the major product), 4.96 (2H, s, for the minor product), 5.96 (1H, t, J=7.5 Hz, for the major product), 6.06 (1H, t, J=7.5 Hz, for the major product), 7.05 (1H Ar, d, J=8 Hz), 7.15 (1H Ar, s), 7.22 to 7.37 (2H Ar, m), 7.44 (1H Ar, s, for the major product), 7.52 (1H Ar, s, for the minor product), 7.83 (1H Ar, d, J=8). $^{13}$C ($CDCl_3$): 14.45 ($CH_3$), 22.63 ( ), 28.76 ( ), 29.58 ( ), 31.54 ( ), 31.65 ( ), 31.96 ($CH_3$ TTN), 31.99 ($CH_3$ TTN), 34.18 (C TTN), 34.31 (C TTN), 35.25 ($CH_2$ TTN), 52.36 ($OCH_3$), 73.83 ($CH_2O$), 93.51 (C—I), 112.98 (CH), 123.31 (CH), 125.77 (CH Ar), 126.36 (CH Ar), 127.19 (CH Ar), 131.48 (CH), 135.19 (C), 139.51 (CH), 143.74 (C), 144.59 (C), 157.45 (C—O Ar), 166.65 (COO).

Methyl 3-(5,6,7,8-tetrahydro-5,5,8,8-tetramethyl-2-naphthyl)-3-(2-hexenyl)-2H-1-benzofuran-6-carboxylate A mixture of tributylamine (0.28 ml, 1.16 mmol), palladium diacetate (24 mg, 0.1 mmol) and methyl 4-iodo-3-[2-(5,6,7,8-tetrahydro-5,5,8,8-tetramethyl-2-naphthyl)-2-octenyloxy]benzoate (610 mg, 1.06 mmol) in acetonitrile (15 ml) is heated at 80° C. for 24 h. The reaction medium is concentrated on a rotary evaporator under vacuum at 40° C. and then treated with 20 ml of water and ethyl ether. After separation of the phases by settling, the organic phase is washed twice with 20 ml of water, dried over magnesium sulphate and concentrated on a rotary evaporator under vacuum at 40° C.

The product is purified by flash chromatography on a column of silica (80% $CH_2Cl_2$, 20% heptane).

Amorphous yellow. Mass: 305 mg. Yield: 64%. $C_{30}H_{38}O_3$ Mw: 446.63 Elemental analysis: Calculated: C: 80.68, H: 8.58. Found: C: 80.52, H: 8.38. MS m/z: 446 (M+). NMR δ ppm: $^1H$ (250 MHz, $CDCl_3$): 0.78 to 0.91 (twice $CH_3$ of the hexyl chains for the two products, m), 1.21 to 1.31 (16H, m, 4 $CH_3$ TTN and 1 $CH_2$), 1.55 to 1.73 (6H, m, 2 $CH_2$ TTN and 1 $CH_2$) 1.83 to 2.12 (2H, m, allylic $CH_2$), 3.90 (O—$CH_3$, s), 4.54–4.65 ($CH_2O$, m), 5.14 to 5.47 (2H ethylenic, m), 7.00 (twice 1H, d, J=8.12 Hz), 7.01 to 7.23 (twice 3H Ar, m), 7.47 (twice 1H Ar, m), 7.61 (twice 1H Ar, m).

Example 27

Process for the preparation of 3-(5,6,7,8-tetrahydro-5,5,8,8-tetramethyl-2-naphthyl)-3-(2-hexenyl)-2H-1-1-benzofuran-6-carboxylic acid The experimental procedure is analogous to that followed in order to obtain Example 2, applied to Example 26.

Yellow amorphous material. Mass: 285 mg, Yield: 80%. $C_{29}H_{36}O_3$ Mw: 432.60; MS m/z: 431 (M+).

Example 28

Process for the preparation of 3-(5,6,7,8-tetrahydro-5,5,8,8-tetramethyl-2-naphthyl)-3-hexyl-2H-1-benzofuran-6-carboxylic acid A solution of the product of Example 27 in ethyl acetate, in the presence of palladium-on-charcoal at a pressure of 6 bar of hydrogen, is stirred at room temperature for 48 h. The mixture is filtered through Celite and then concentrated on a rotary evaporator under vacuum at 40° C.

The product is purified by crystallization from $CH_3CN$.

White solid. Mass: 125 mg. Yield: 45%. m.p.=137° C.; $C_{29}H_{38}O_3$ Mw: 434.62 Elemental analysis: Calculated: C: 80.14, H: 8.81, O: 11.04. Found: C: 79.72, H: 8.71, 0: 10.67. MS m/z: 433 (M+). IR ($cm^{-1}$): 1292=C—O, 1441 C=C, 1687 C=O, 2931–2963 C—H. NMR δ ppm: $^1H$ (250 MHz, $CDCl_3$): 0.85 (3H, t, J=8.7 Hz), 1.20 to 1.26 (20H, m), 1.67 (4H, s), 2.09 (2H, t, J=7 Hz), 4.60 (2H, s), 7.00 (1H, d, J=8.3 Hz), 7.15 to 7.25 (3H Ar, m), 7.56 (1H Ar, s), 7.71 (1H Ar, d, J=7.8 Hz). $^{13}C$ (250 MHz, $CDCl_3$): 13.88 ($CH_3$), 22.47 ($CH_2$), 24.42 ($CH_2$), 29.63 ($CH_2$), 31.52 ($CH_2$), 31.66 ($CH_3$ TTN), 31.78 ($CH_3$ TTN), 33.85 (C TTN), 34.26 (C TTN), 34.93 ($CH_2$ TTN), 35.01 ($CH_2$ TTN), 38.87 ($CH_2$), 53.79 (C), 84.57 ($CH_2O$), 111.16 (CH Ar), 122.99 (CH Ar), 123.80 (CH Ar), 124.47 (CH Ar), 126.55 (CH Ar), 129.49 (C Ar), 140.25 (C Ar), 143.12 (C Ar), 144.78 (C Ar), 160.29 (C—O Ar), 171.64 (COO).

Example 29

Process for the preparation of methyl 3-methoxycarbonylmethyl-3-(5,5,8,8-tetramethyl-5,6,7,8-tetrahydronaphth-2-yl)-2H-1-benzofuran-6-carboxylate
Methyl 4-iodo-3-[3-methoxycarbonyl-2-(5,5,8,8-tetramethyl-5,6,7,8-tetrahydronaphth-2-yl)allyloxy] benzoate The experimental procedure is similar to that followed in order to obtain methyl 4-iodo-3-[2-(5,6,7,8-tetrahydro-5,5,8,8-tetramethyl-2-naphthyl)-1-propenyloxy]benzoate, applied to the product methyl 3-[(5,6,7,8-tetrahydro-5,5,8,8-tetramethyl-2-naphthoyl)-methyloxy]-4-iodobenzoate and trimethyl phosphono-acetate.

White solid. Mass: 225 mg. Yield: 12%. m.p.=115° C.; $C_{27}H_{31}O_5$ Mw: 561.9. Elemental analysis: Calculated: C: 57.66, H: 5.56. Found: C: 57.25, H: 5.68. NMR δ ppm: $^1H$ (250 MHz, $CDCl_3$): 1.28 (6H, s, $CH_3$ TTN), 1.30 (6H, s, $CH_3$ TTN), 1.70 (4H, s, $CH_2$ TTN), 3.59 (3H, s, O—$CH_3$), 3.91 (3H, s, O—$CH_3$), 4.83 (2H, s), 6.50 (1H, s), 7.07 (1H Ar, d, J=8.2 Hz), 7.22 (1H Ar, s), 7.33 (1H Ar, d, J=8 Hz), 7.40 to 7.43 (2H Ar, m), 7.89 (1H Ar, d, J=8.2). $^{13}C$ (250 MHz, $CDCl_3$): 32.21 ($CH_3$ TTN), 34.59 (C TTN), 34.66 (C TTN), 35.41 ($CH_2$ TTN), 51.61 ($OCH_3$), 52.71 ($OCH_3$), 71.97 ($CH_2O$), 93.99 (C—I), 112.81 (CH), 117.30 (CH), 124.28 (CH), 124.84 (CH), 126.70 (CH), 132.01 (C), 133.32 (C), 140.07 (CH Ar), 145.09 (C), 145.76 (C), 151.91 (C), 155.94 (C Ar), 166.65 (COO), 166.74 (COO).

Methyl 3-methoxycarbonylmethyl-3-(5,5,8,8-tetramethyl-5,6,7,8-tetrahydronaphth-2-yl)-2H-1-benzofuran-6-carboxylate The experimental procedure is similar to that followed in order to obtain Example 3, applied to the above product. The product is purified by flash chromatography on a column of silica (80% $CH_2Cl_2$, 20% heptane).

Amorphous white product. Mass: 88 mg. Yield: 59%. $C_{27}H_{32}O_5$ Mw: 436.55. Elemental analysis: Calculated: C: 74.29, H: 7.39. Found: C: 74.27, H: 7.28. MS m/z: 436 (M+). NMR δ ppm: $^1H$ ($CDCl_3$): 1.19 (6H, s, $CH_3$ TTN), 1.22 (6H, s, $CH_3$ TTN), 1.64 (4H, s, $CH_2$ TTN), 3.03 (1H, d, J=15 Hz), 3.31 (1H, d, J=15 Hz), 3.58 (3H, s, O—$CH_3$), 3.90 (3H, s, O—$CH_3$), 4.81 (1H, d, J=17 Hz), 4.92 (1H, d, J=17 Hz), 6.96 (1H Ar, d, J=7.5 Hz), 7.14 to 7.21 (3H Ar, m), 7.50 (1H Ar, s), 7.60 (1H Ar, d, J=8.00 Hz). $^{13}C$ ($CDCl_3$): 32.06 ($CH_3$ TTN), 32.16 ($CH_3$ TTN), 32.20 ($CH_3$ TTN), 34.30 (C TTN), 34.72 (C TTN), 35.33 ($CH_2$ TTN), 35.40 ($CH_2$ TTN), 43.24 ($CH_2$), 52.00 (C), 52.08 ($OCH_3$), 52.48 ($OCH_3$), 84.55 ($CH_2O$), 111.40 (CH Ar), 122.98 (CH Ar), 123.59 (CH Ar), 123.98 (CH Ar), 124.97 (CH Ar), 127.27 (CH Ar), 131.42 (C Ar), 138.78 (C Ar), 140.75 (C Ar), 143.96 (C Ar), 145.35 (C Ar), 160.07 (C—O Ar), 167.19 (COO), 171.36 (COO).

Example 30

Process for the Preparation of 3-carboxymethyl-3-(5,5,8,8-tetramethyl-5,6,7,8-tetrahydronaphth-2-yl)-2H-1-benzofuran-6-carboxylic acid The experimental procedure is similar to that followed in order to obtain Example 2, applied to the product of Example 29.

White powder. Mass: 51 mg. Yield: 71%. m.p.=268° C. $C_{25}H_{28}O_5$ Mw: 408.50 Elemental analysis: Calculated: C: 73.51, H: 6.91. Found: C: 72.37, H: 6.88. MS m/z: 407 (M+). IR ($cm^{-1}$): 1258–1280=C—O, 1411–1435 C=C, 1699 C=O, 2925 C—H. NMR δ ppm: $^1H$ (DMSO): 1.19 (12H, s, $CH_3$ TTN), 1.21 (6H, s, $CH_3$ TTN), 1.52 (4H, s, $CH_2$ TTN), 3.06 (1H, d, J=16 Hz), 3.54 (1H, d, J=16 Hz), 4.83 (1H, d, J=10 Hz), 5.01 (1H, d, J=10 Hz), 7.04 (1H Ar, d, J=8.3 Hz), 7.21 (1H Ar, d, J=8.3 Hz), 7.29 to 7.31 (2H Ar, m), 7.36 (1H Ar, d, J=7.8 Hz), 7.47 (1H Ar, d, J=7.8 Hz). $^{13}C$ (DMSO): 31.52 ($CH_3$ TTN), 31.60 ($CH_3$ TTN), 33.61 (C TTN), 34.07 (C TTN), 34.61 ($CH_2$ TTN), 42.31 ($CH_2$), 50.63 (C), 83.44 ($CH_2O$), 110.06 (CH Ar), 122.28 (CH Ar), 122.86 (CH Ar), 123.13 (CH Ar), 124.59 (CH Ar), 126.57 (CH Ar), 131.40 (C Ar), 139.45 (C Ar), 141.45 (C Ar), 142.63 (C Ar), 144.31 (C Ar), 158.77 (C—O Ar), 167.03 (COO), 172.09 (COO).

B. FORMULATION EXAMPLES

1) ORAL ROUTE (a) The following composition is prepared in the form of a 0.8 g tablet

| | |
|---|---|
| Compound of Example 1 | 0.005 g |
| Pregelatinized starch | 0.265 g |
| Microcrystalline cellulose | 0.300 g |
| Lactose | 0.200 g |
| Magnesium stearate | 0.030 g |

For the treatment of acne, 1 to 3 tablets are administered to an adult individual per day for 3 to 6 months, depending on the seriousness of the case treated.

(b) A drinkable suspension intended to be packaged in 5 ml ampules is prepared

| | |
|---|---|
| Compound of Example 2 | 0.050 g |
| Glycerol | 0.500 g |
| 70% sorbitol | 0.500 g |
| Sodium saccharinate | 0.010 g |
| Methyl para-hydroxybenzoate | 0.040 g |
| Flavouring qs | |
| Purified water qs | 5 ml |

For the treatment of acne, 1 ampule is administered to an adult individual per day for 3 months depending on the seriousness of the case treated.

(c) The following formula intended to be packaged as gelatin capsules is prepared:

| | |
|---|---|
| Compound of Example 3 | 0.025 g |
| Corn starch | 0.060 g |
| Lactose qs | 0.300 g |

The gelatin capsules used consist of gelatin, titanium oxide and a preserving agent.

In the treatment of psoriasis, 1 gelatin capsule is administered to an adult individual per day for 30 days.

2) TOPICAL ROUTE (a) The following nonionic water-in-oil cream is prepared:

| | |
|---|---|
| Compound of Example 4 | 0.100 g |
| Mixture of emulsifying lanolin alcohols, refined oils and waxes, sold by the company BDF under the name "anhydrous eucerin" | 39.900 g |
| Methyl para-hydroxybenzoate | 0.075 g |
| Propyl para-hydroxybenzoate | 0.075 g |
| Sterile demineralized water qs | 100.000 g |

This cream is applied to psoriatic skin 1 to 2 times a day for 30 days.

(b) A gel is prepared by producing the following formulation:

| | |
|---|---|
| Compound of Example 5 | 0.050 g |
| Erythromycin base | 4.000 g |
| Butylhydroxytoluene | 0.050 g |
| Hydroxypropylcellulose sold by the company Hercules under the name "Klucel HF" | 2.000 g |
| Ethanol (95°) qs | 100.000 g |

This gel is applied to skin attacked by dermatitis or to acneic skin 1 to 3 times a day for 6 to 12 weeks depending on the seriousness of the case treated.

(c) An anti-seborrhoea lotion is prepared by mixing together the following ingredients:

| | |
|---|---|
| Compound of Example 6 | 0.030 g |
| Propylene glycol | 5.000 g |
| Butylhydroxytoluene | 0.100 g |
| Ethanol (95°) qs | 100.000 g |

This lotion is applied twice a day to a seborrhoeic scalp and a significant improvement is observed within 2 to 6 weeks.

(d) A cosmetic composition to combat the harmful effects of sunlight is prepared by mixing together the following ingredients:

| | |
|---|---|
| Compound of Example 7 | 1.000 g |
| Benzylidenecamphor | 4.000 g |
| Fatty acid triglycerides | 31.000 g |
| Glyceryl monostearate | 6.000 g |
| Stearic acid | 2.000 g |
| Cetyl alcohol | 1.200 g |
| Lanolin | 4.000 g |
| Preserving agents | 0.300 g |
| Propylene glycol | 2.000 g |
| Triethanolamine | 0.500 g |
| Fragrance | 0.400 g |
| Demineralized water qs | 100.000 g |

This composition is applied daily and makes it possible to combat light-induced ageing.

(e) The following nonionic oil-in-water cream is prepared:

| | |
|---|---|
| Compound of Example 8 | 0.500 g |
| Vitamin D3 | 0.020 g |
| Cetyl alcohol | 4.000 g |
| Glyceryl monostearate | 2.500 g |
| PEG-50 stearate | 2.500 g |
| Karite butter | 9.200 g |
| Propylene glycol | 2.000 g |
| Methyl para-hydroxybenzoate | 0.075 g |
| Propyl para-hydroxybenzoate | 0.075 g |
| Sterile demineralized water qs | 100.000 g |

This cream is applied to psoriatic skin 1 to 2 times a day for 30 days.

(f) A topical gel is prepared by mixing together the following ingredients:

| | |
|---|---|
| Compound of Example 9 | 0.050 g |
| Ethanol | 43.000 g |
| α-Tocopherol | 0.050 g |
| Carboxyvinyl polymer sold under the name Carbopol 941" by the company "Goodrich" | 0.500 g |
| Triethanolamine as an aqueous 20% by weight solution | 3.800 g |
| Water | 9.300 g |
| Propylene glycol qs | 100.00 g |

This gel is applied in the treatment of acne 1 to 3 times a day for 6 to 12 weeks depending on the seriousness of the case treated.

(g) A lotion to prevent hair loss and promote regrowth of the hair is prepared by mixing together the following ingredients:

|  |  |
|---|---|
| Compound of Example 10 | 0.05 g |
| Compound sold under the name "Minoxidil" | 1.00 g |
| Propylene glycol | 20.00 g |
| Ethanol | 34.92 g |
| Polyethylene glycol (molecular mass = 400) | 40.00 g |
| Butylhydroxyanisole | 0.01 g |
| Butylhydroxytoluene | 0.02 g |
| Water qs | 100.00 g |

This lotion is applied twice a day for 3 months to a scalp which has lost a considerable amount of hair.

(h) An anti-acne cream is prepared by mixing together the following ingredients:

|  |  |
|---|---|
| Compound of Example 6 | 0.050 g |
| Retinoic acid | 0.010 g |
| Mixture of glyceryl stearate and polyethylene glycol stearate (75 mol) sold under the name "Gelot 64" by the company "Gattefosse" | 15.000 g |
| Core oil polyoxyethylenated with 6 mol of ethylene oxide, sold under the name "Labrafil M2130 CS" by the company "Gattefosse" | 8.000 g |
| Perhydrosqualene | 10.000 g |
| Preserving agents | qs |
| Polyethylene glycol (molecular mass = 400) | 8.000 g |
| Disodium salt of ethylenediaminetetraacetic acid | 0.050 g |
| Purified water qs | 100.000 g |

This cream is applied to skin attacked by dermatitis or to acneic skin 1 to 3 times a day for 6 to 12 weeks.

(i) An oil-in-water cream is prepared by producing the following formulation:

|  |  |
|---|---|
| Compound of Example 5 | 0.020 g |
| Betamethasone 17-valerate | 0.050 g |
| S-Carboxymethylcysteine | 3.000 g |
| Polyoxyethylene stearate (40 mol of ethylene oxide) sold under the name "Myrj 52" by the company "Atlas" | 4.000 g |
| Sorbitan monolaurate, polyoxyethylenated with 20 mol of ethylene oxide, sold under the name "Tween 20" by the company "Atlas" | 1.800 g |
| Mixture of glyceryl monostearate and glyceryl distearate, sold under the name "Geléol" by the company "Gattefosse" | 4.200 g |
| Propylene glycol | 10.000 g |
| Butylhydroxyanisole | 0.010 g |
| Butylhydroxytoluene | 0.020 g |
| Cetostearyl alcohol | 6.200 g |
| Preserving agents | qs |
| Perhydrosqualene | 18.000 g |
| Mixture of caprylic/capric triglycerides sold under the name "Miglyol 812" by the company "Dynamit Nobel" | 4.000 g |
| Triethanolamine (99% by weight) | 2.500 g |
| Water qs | 100.000 g |

This cream is applied twice a day to skin attacked by dermatitis, for 30 days.

(j) The following cream of oil-in-water type is prepared:

|  |  |
|---|---|
| Lactic acid | 5.000 g |
| Compound of Example 2 | 0.020 g |
| Polyoxyethylene stearate (40 mol of ethylene oxide) sold under the name "Myrj 52" by the company "Atlas" | 4.000 g |
| Sorbitan monolaurate, polyoxyethylenated with 20 mol of ethylene oxide, sold under the name "Tween 20" by the company "Atlas" | 1.800 g |
| Mixture of glyceryl monostearate and glyceryl distearate, sold under the name "Geleol" by the company "Gattefosse" | 4.200 g |
| Propylene glycol | 10.000 g |
| Butylhydroxyanisole | 0.010 g |
| Butylhydroxytoluene | 0.020 g |
| Cetostearyl alcohol | 6.200 g |
| Preserving agents | qs |
| Perhydrosqualene | 18.000 g |
| Mixture of caprylic/capric triglycerides sold under the name "Miglyol 812" by the company "Dynamit Nobel" | 4.000 g |
| Water qs | 100.000 g |

This cream is applied once a day and helps to combat both light-induced and chronological ageing.

We claim:

1. A heterocyclic compound, as set fourth in formula (I) below:

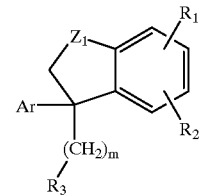

(I)

in which:

Ar represents
either the radical of formula (II) below:

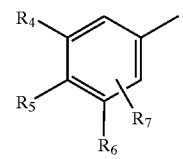

(II)

or the radical of formula (III) below:

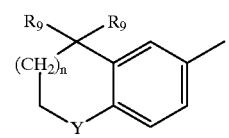

(III)

or the radical of formula (IV) below:

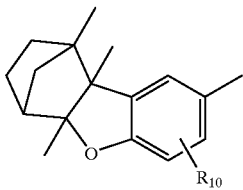

(IV)

$R_1$ represents an atom or a radical chosen from
(i) the —$CH_3$ radical,
(ii) the radical —$(CH_2)_p$—O—$R_{11}$,
(iii) a radical —$OR_{11}$,
(iv) a radical

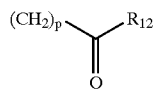

(v) a radical —$S(O)_tR_{13}$,
$R_{11}, R_{12}, R_{13}$, p and t having the meanings given below,
$R_2$ represents a hydrogen atom, a halogen atom, an alkyl radical or the radical —$OR_{11}$,
$R_{11}$ having the meaning given below,
$R_3$ represents an atom or a radical chosen from:
(i) an atom or a radical chosen from a hydrogen atom, an alkyl radical, an alkenyl radical, an alkynyl radical, an aryl radical, a monohydroxyalkyl or polyhydroxyalkyl radical, a polyether radical, a cyano radical or a radical —O—$R_{11}$,
$R_{11}$ having the meaning given below,
(ii) a radical

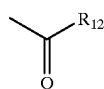

$R_{12}$ having the meaning given below,
(iii) a radical

r and r' having the meaning given below,
$Z_1$ represents O, S or NR',
m is an integer between 0 and 10,
it being understood in all of the preceding text that:
$R_4, R_5, R_6$ and $R_7$, which may be identical or different, are chosen from:
(i) a hydrogen atom,
(ii) an alkyl radical having at least 4 carbon atoms, wherein the carbon attached to the phenyl radical is substituted with at least two carbon atoms,
(iii) a cycloalkyl radical,
(iv) a radical —$(Z_2)_n$—$(CH_2)_q$—CO—$R_{12}$,
(v) a radical —$Z_3$—$R_{11}$,
with the proviso that at least of the radicals $R_4, R_5, R_6$ and $R_7$ is an alkyl radical as defined in (ii) or a cycloalkyl radical (iii), $Z_2, Z_3, R_{11}, R_{12}$, n and q having the meanings given below,
$R_8$ and $R_9$ represent lower alkyl radicals,
$R_{10}$ represents a lower alkyl radical, a radical —$OR_{11}$ or a polyether radical,
$R_{11}$, which may be identical or different, represents a hydrogen atom, a lower alkyl radical, an aryl radical, an aralkyl radical, a monohydroxyalkyl or polyhydroxyalkyl radical, a polyether radical or a lower acyl radical,
$R_{12}$, which may be identical or different, represents:
(a) a hydrogen atom, an alkynyl radical, an alkenyl radical, an alkyl radical or a heterocycle,
(b) a radical

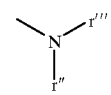

r" and r'" having the meaning given below
(c) a radical —$OR_{13}$
$R_{13}$, which may be identical or different, represents a hydrogen atom, an alkyl radical, a monohydroxyalkyl or polyhydroxyalkyl radical, an optionally substituted aryl or aralkyl radical or a sugar, amino acid or peptide residue,
R', which may be identical or different, represents a protecting group for amine functions, a hydrogen atom, a lower alkyl radical, a polyether radical or an optionally substituted aryl radical or an amino acid, peptide or sugar residue,
r and r', which may be identical or different, represent protecting groups for amine functions, a hydrogen atom, a lower alkyl radical, a polyether radical, an optionally substituted aryl radical or an amino acid, peptide or sugar residue, or alternatively, taken together, form a heterocycle,
r" and r'", which may be identical or different, represent a hydrogen atom, a lower alkyl radical, a polyether radical, an optionally substituted aryl radical or an amino acid, peptide or sugar residue, or alternatively, taken together, form a heterocycle,
Y represents $C(R_9)_2$, O, S, Nr', CHOH, CO, SO or $SO_2$,
$Z_2$ represents O, S or NR',
$Z_3$ represents O or S,
n, which may be identical or different, is equal to 0 or 1;
p, which may be identical or different, is equal to 0, 1, 2 or 3; t is equal to 0, 1, 2 or 3; q is an integer between 0 and 10 or a salt or an isomer thereof.

2. A heterocyclic biaryl compound or salt according to claim 1.

3. The salt according to claim 2, which is the salt of an organic or inorganic acid.

4. The salt according to claim 2, wherein said salt contains an alkali metal cation, an alkaline-earth metal cation, or a zinc cation.

5. A compound according to claim 1, wherein the alkyl radical is selected from the group consisting of methyl, ethyl, isopropyl, butyl, tert-butyl, hexyl, nonyl and dodecyl.

6. A compound according to claim 1, wherein the polyhydroxyalkyl radical is selected from the group consisting of 2,3-dihydroxypropyl, 2,3,4-trihydroxybutyl, 2,3,4,5-tetrahydroxypentyl, and pentaerythritol.

7. A compound according to claim 1, wherein the aryl radical is a phenyl radical which optionally is substituted with the moiety selected from the group consisting of a halogen, a hydroxyl, an alkyl, a nitro, a methoxy, and a substituted amine group.

8. A compound according to claim 1, wherein the aralkyl radical is selected from the group consisting of benzyl and phenethyl radicals which optionally are substituted with at least one moiety selected from the group consisting of a halogen atom, a hydroxyl group, a nitro group, and a methoxy group.

9. A compound according to claim 1, wherein the alkenyl radical comprises one to five carbon atoms and has one or two sites of unsaturation.

10. A compound according to claim 1, wherein the sugar residue is a monosaccharide selected from the group consisting of glucose, galactose, mannose and glucuronic acid.

11. A compound according to claim 1, wherein the amino acid residue is selected from the group consisting of lysine, glycine, and aspartic acid.

12. A compound according to claim 1, wherein the peptide residue is a dipeptide or a tripeptide.

13. A compound according to claim 1, wherein the heterocyclic radical is selected from the group consisting of piperidino, morpholino, pyrrolidino, and piperazino, wherein said heterocyclic radical is optionally substituted at position 4 with a $C_1$–$C_6$ alkyl or a polyhydroxyalkyl radical.

14. A compound according to claim 1, wherein the halogen atom is fluorine or chlorine.

15. A compound according to claim 1, wherein the aminoalkyl radical is selected from the group consisting of aminomethyl, 3-aminopropyl, and 6-aminohexyl.

16. A compound according to claim 1, wherein the alkynyl radical has 2 to 6 carbon atoms.

17. A compound according to claim 1, wherein the cycloaliphatic radical has 3 to 6 carbon atoms.

18. A compound according to claim 17, wherein said cycloaliphatic radical is a cyclopropyl or cyclohexyl.

19. A compound according to claim 1, wherein the lower acyl radical is selected from the group consisting of acetyl, propionyl and pivaloyl.

20. A compound according to claim 1, wherein the cycloalkyl radical is an adamantyl or 1-methylcyclohexyl.

21. A compound according to claim 1, wherein the polyether radical is selected from the group consisting of methoxymethyl ether, methoxyethoxymethyl ether, and methylthiomethyl ether.

22. A compound according to claim 1, which is selected from the group consisting of:

3-[3-(1-adamantyl)-4-methoxyphenyl]-3-methyl-2H-1-benzofuran-6-carboxylic acid, methyl 3-[3-(1-adamantyl)-4-methoxyphenyl]-3-methyl-2H-1-benzofuran-6-carboxylate, 3-[3-(1-adamantyl-4-methoxyphenyl)]-3-methyl-2H-1-benzofuran-5-carboxylic acid, methyl 3-[3-(1-adamantyl)-4-methoxyphenyl)]-3-methyl-2H-1-benzofuran-5-carboxylate, 3-methyl-3-(5,6,7,8-tetrahydro-5,5,8,8-tetramethyl-2-naphthyl)-2H-1-benzofuran-6-carboxylic acid, methyl 3-methyl-3-(5,6,7,8-tetrahydro-5,5,8,8-tetramethyl-2-naphthyl)-2H-1-benzofuran-6-carboxylate, 3-(propen-2-yl)-3-(5,6,7,8-tetrahydro-5,5,8,8-tetramethyl-2-naphthyl)-2H-1-benzofuran-6-carboxylic acid methyl 3-(propen-2-yl)-3-(5,6,7,8-tetrahydro-5,5,8,8-tetramethyl-2-naphthyl)-2H-1-benzofuran-6-carboxylate, 3-(propen-2-yl)-3-(5,6,7,8-tetrahydro-5,5,8,8-tetramethyl-2-naphthyl)-2H-1-benzofuran-5-carboxylic acid methyl 3-(propen-2-yl)-3-(5,6,7,8-tetrahydro-5,5,8,8-tetramethyl-2-naphthyl)-2H-1-benzofuran-5-carboxylate, 3-methyl-3-(5,6,7,8-tetrahydro-5,5,8,8-tetramethyl-2-naphthyl)-2H-1-benzofuran-5-carboxylic acid, methyl 3-methyl-3-(5,6,7,8-tetrahydro-5,5,8,8-tetramethyl-2-naphthyl)-2H-1-benzofuran-5-carboxylate, 3-methyl-3-(1,2,3,4-tetrahydro-1,4a,9b-trimethyl-1,4-methanodibenzofur-8-yl)-2H-1-benzofuran-6-carboxylic acid, methyl 3-methyl-3-(1,2,3,4-tetrahydro-1,4a,9b-trimethyl-1,4-methanodibenzofur-8-yl)-2H-1-benzofuran-6-carboxylate, 3-methyl-3-(1,2,3,4-tetrahydro-1,4a,9b-trimethyl-1,4-methanodibenzofur-8-yl)-2H-1-benzofuran-5-carboxylic acid, methyl 3-methyl-3-(1,2,3,4-tetrahydro-1,4a,9b-trimethyl-1,4-methanodibenzofur-8-yl)-2H-1-benzofuran-5-carboxylate, 3-allyl-3-(5,6,7,8-tetrahydro-5,5,8,8-tetramethyl-2-naphthyl)-2H-1-benzofuran-6-carboxylic acid, methyl 3-allyl-3-(5,6,7,8-tetrahydro-5,5,8,8-tetramethyl-2-naphthyl)-2H-1-benzofuran-6-carboxylate,

[3-(5,6,7,8-tetrahydro-5,5,8,8-tetramethyl-2-naphthyl)-3-methyl-2H-1-benzofur-5-oyl]morpholine, N-4-hydroxyphenyl-3-(5,6,7,8-tetrahydro-5,5,8,8-tetramethyl-2-naphthyl)-3-methyl-2H-1-benzofuran-5-carboxamide, N-butyl-3-methyl-3-(5,5,8,8-tetramethyl-5,6,7,8-tetrahydro-2-naphthyl)-2H-1-benzofuran-5-carboxamide, methyl 3-[4-(1-adamantyl)-3-methoxyphenyl-3-methyl-2H-1-benzofuran]-6-carboxylate, 3-[4-(1-adamantyl)-3-methoxyphenyl-3-methyl-2H-1-benzofuran]-6-carboxylic acid, methyl 3-(3-methyl-5,6,7,8-tetrahydro-5,5,8,8-tetramethyl-2-naphthyl)-3-methyl-2H-1-benzofuran-6-carboxylate, 3-(3-methyl-5,6,7,8-tetrahydro-5,5,8,8-tetramethyl-2-naphthyl)-3-methyl-2H-1-benzofuran-6-carboxylic acid, methyl 3-(5,6,7,8-tetrahydro-5,5,8,8-tetramethyl-2-naphthyl)-3-(3,5-di-tert-butyl-4-hydroxybenzyl)-2H-1-benzofuran-6-carboxylate, 3-(5,6,7,8-tetrahydro-5,5,8,8-tetramethyl-2-naphthyl)-3-(3,5-di-tert-butyl-4-hydroxybenzyl)-2H-1-benzofuran-6-carboxylic acid, 3-(5,6,7,8-tetrahydro-5,5,8,8-tetramethyl-2-naphthyl)-3-methyl-2H-1-benzofuran-5-methanol, 3-(5,6,7,8-tetrahydro-5,5,8,8-tetramethyl-2-naphthyl)-3-methyl-2H-1-benzofuran-5-carbaldehyde, methyl (−)-3-(5,6,7,8-tetrahydro-5,5,8,8-tetramethyl-2-naphthyl)-3-methyl-2H-1-benzofuran-5-carboxylate, methyl (+)-3-(5,6,7,8-tetrahydro-5,5,8,8-tetramethyl-2-naphthyl)-3-methyl-2H-1-benzofuran-5-carboxylate, methyl (−)-3-(5,6,7,8-tetrahydro-5,5,8,8-tetramethyl-2-naphthyl)-3-methyl-2H-1-benzofuran-6-carboxylate, methyl (+)-3-(5,6,7,8-tetrahydro-5,5,8,8-tetramethyl-2-naphthyl)-3-methyl-2H-1-benzofuran-6-carboxylate, methyl 3-(5,6,7,8-tetrahydro-5,5,8,8-tetramethyl-2-naphthyl)-3-(2-hexenyl)-2H-1-benzofuran-6-carboxylate, 3-(5,6,7,8-tetrahydro-5,5,8,8-tetramethyl-2-naphthyl)-3-(2-hexenyl)-2H-1-benzofuran-6-carboxylic acid, 3-(5,6,7,8-tetrahydro-5,5,8,8-tetramethyl-2-naphthyl)-3-hexyl-2H-1-benzofuran-6-carboxylic acid, methyl 3-methoxycarbonylmethyl-3-(5,5,8,8-tetramethyl-5,6,7,8-tetrahydro-2-naphthyl)-2H-1-benzofuran-6-carboxylate, 3-carboxymethyl-3-(5,5,8,8-tetramethyl-5,6,7,8-tetrahydro-2-naphthyl)-2H-1-benzofuran-6-carboxylic acid.

23. A compound according to claim 1, having at least one of the following characteristics:

$R_1$ is a radical $-(CH_2)_p-CO-O-R_{13}$ $R_2$ is a hydrogen $R_3$ is a hydrogen or an alkenyl radical $R_5$ or $R_6$ is a radical $-OR_{11}$ $R_7$ is a cycloalkyl radical $Z_1$ is an oxygen atom Y is a radical $C(R_9)_2$ m is equal to 1.

24. A pharmaceutical composition which comprises a pharmaceutically acceptable amount of at least one compound according to claim 1 and a pharmaceutically acceptable carrier.

25. A composition according to claim 24, wherein the concentration of said compound ranges from 0.001% to 5% by weight relative to the weight of the composition as a whole.

26. A cosmetic composition which comprises a cosmetically acceptable amount of a compound according to claim 1, and a cosmetically acceptable carrier.

27. The cosmetic composition according to claim 26, wherein the concentration of said compound ranges from 0.001% to 3% by weight relative to the weight of the composition as a whole.

* * * * *